(12) United States Patent
Hutchinson et al.

(10) Patent No.: US 6,872,971 B2
(45) Date of Patent: Mar. 29, 2005

(54) SCAFFOLD-ORGANIZED CLUSTERS AND ELECTRONIC MADE USING SUCH CLUSTERS

(75) Inventors: James E. Hutchinson, Eugene, OR (US); Scott M. Reed, Eugene, OR (US); Martin N. Wybourne, Hanover, NH (US)

(73) Assignee: The State of Oregon acting by and through the State Board of Higher Education on behalf of The University of Oregon, Eugene, OR (US)

( * ) Notice: Subject to any disclaimer, the term of this patent is extended or adjusted under 35 U.S.C. 154(b) by 0 days.

(21) Appl. No.: 10/783,515

(22) Filed: Feb. 19, 2004

(65) Prior Publication Data

US 2004/0166673 A1 Aug. 26, 2004

Related U.S. Application Data

(62) Division of application No. 09/817,708, filed on Mar. 26, 2001, now Pat. No. 6,730,537.
(60) Provisional application No. 60/231,193, filed on Sep. 7, 2000, provisional application No. 60/226,720, filed on Aug. 21, 2000, and provisional application No. 60/191,814, filed on Mar. 24, 2000.

(51) Int. Cl.[7] .......................... H01L 35/24; H01L 51/00
(52) U.S. Cl. .............................. 257/40; 257/E51.045; 257/798
(58) Field of Search ......................... 257/40, E51.045, 257/619, 798

(56) References Cited

U.S. PATENT DOCUMENTS

| | | |
|---|---|---|
| 4,522,932 A | 6/1985 | Mitchell, III |
| 5,156,810 A | 10/1992 | Ribi |
| 5,242,877 A | 9/1993 | Dobson et al. |
| 5,389,401 A | 2/1995 | Gordon |
| 5,521,289 A | 5/1996 | Hainfeld et al. |
| 5,536,858 A | 7/1996 | LaLonde et al. |
| 5,578,248 A | 11/1996 | Hattori et al. |
| 5,952,172 A | 9/1999 | Meade et al. |
| 5,952,472 A | 9/1999 | Hanai et al. ............. 530/387.1 |
| 6,121,425 A | 9/2000 | Hainfeld et al. |
| 6,730,537 B2 | 5/2004 | Hutchison et al. |
| 2002/0146742 A1 | 10/2002 | Wybourne et al. |

FOREIGN PATENT DOCUMENTS

| | | |
|---|---|---|
| EP | WO98/53841 | 12/1998 |
| WO | WO 94/03496 | 2/1994 |

OTHER PUBLICATIONS

Wybourne et al. "Coulomb–Blockade Dominated Transport in Patterned Gold Structures" Jpn. J. Appl. Phys. vol. 36(1997)Pt. 1, No. 23B, pp7796–7800. Dec. 1997.*

Alivisatos, A., et al., Organization of 'Nanocrystal Molecules' using DNA, *Nature*, 382:609–611, 1996.

(Continued)

*Primary Examiner*—Craig A. Thompson
(74) *Attorney, Agent, or Firm*—Klarquist Sparkman, LLP

(57) ABSTRACT

A method for forming arrays of metal, alloy, semiconductor or magnetic clusters is described. The method comprises placing a scaffold on a substrate, the scaffold comprising, for example, polynucleotides and/or polypeptides, and coupling the clusters to the scaffold. Methods of producing arrays in predetermined patterns and electronic devices that incorporate such patterned arrays are also described.

3 Claims, 16 Drawing Sheets

OTHER PUBLICATIONS

Andres, R., et al., 'Coulomb Staircase' at Room Temperature in a Self-assembled Molecular Nanostructure, *Science* 272:1323–1325, 1996.

Andres, R., et al., Self-Assembly of a Two-Dimensional Superlattice of Molecularly Linked Metal Clusters, *Science*, 273:1690–1693, 1996.

Applicants co-pending U.S. Appl. No. 09/085,390, filed May 27, 1995, Scaffold-Organized Metal, Alloy, Semiconductor, and/or Magnetic Lusters and Electronic Devices Made Using Such Clusters.

Braun, E., et al.. DNA–Templated Assembly and Electrode Attachment of a Conducting Silver Wire, *Nature*, 391:775–778, 1998.

Brown, L. and Hutchison, J., Convenient Preparation of Stable, Narrow–Dispersity, Gold Nanocrystals by Ligand Exchange Reactions, *J. Am. Chem. Soc.*, 119:12384–12385, 1997.

Brust, M., et al., Novel Gold–dithiol Nano–networks with Non–mettalic Electronic Properties, *Adv. Mater.*, 7:795–797, 1995.

Clarke, L., et al., Fabrication and Near–room Temperature Transport of Patterned Gold Cluster Structures, *J. Vac. Sci. Technol. B*, 15:2925–2929, 1997.

Feldheim, D., et al., Electron Transfer in Self–Assembled Inorganic Polyelectrolyte/Metal Nanoparticle Heterostructures, *J. Am. Chem. Soc.*, 118:7640–7641, 1996.

Geerligs, L., et al., Frequency–Locked Turnstile Device for Single Electrons, *Phys. Rev. Lett.*, 64:2691–2694, 1990.

Grabar, K., et al., Preparation and Characterization of Au Colloid Monolayers, *Anal. Chem.*, 67:735–743, 1995.

Itou, S., Reorientation of Poly–γ–Benzyl L–Glutamate Liquid Crystals in an Electric Field, *Jpn. J. Appl. Phys.*, 24:1234–1235, 1985.

James J. Storhoff and Chad A. Mirkin, "Programmed Materials Synthesis with DNA," American Chemical Society, pp. 1849–1862 (1999).

Likharev, K., Correlated Discrete Transfer of Single Electrons in Ultrasmall Tunnel Junctions, *IBM J. Res. Dev.*, 32:144–158, 1988.

Mirkin, C., et al., A DNA Based Method for Rationally Assembling Nanoparticles into Macroscopic Materials, *Nature*, 382:607–609, 1996.

Niemeyer, C., DNA as a Material for Nanotechnology, *Angew. Chem., Int. Ed. Engl.*, 36:585–587, 1997.

O'Konski, C., et al., Electric Properties of Macromolecules. IV. Determination of Electric and Optical Parameters From Saturation of Electric Birefringence in Solutions, *J. Phys. Chem.*, 63:1558–1565, 1959.

Osifchin, R., et al., Synthesis of a Quantum Dot Superlattice using Molecularly Linked Metal Clusters, *Superlattices and Microstructures*, 18:283–289, 1995.

Peschel, S. and Schmid, G., First Step Towards Ordered Monolayers of Ligand–Stabilized Gold Clusters, *Angew Chem. Int. Ed. Engl.*, 34:1442–1443, 1995.

Pothier, H., et al., Single–Electron Pump Based on Charging Effects, *Europhys. Lett.*, 17:249–254, 1992.

Qi, J. et al., Ligation of Triangles Built from Bulged 3–Arm DNA Branched Junctions, *J. Am. Chem. Soc.*, 118:6121–6130, 1996.

Schmid, G., Hexachlorododecakis(triphenylphosphine)pentapentacontagold, $Au_{55}[P(C_6H_5)_3]_{12}Cl_6$, *Inorg. Syn.*, 27:214–218, 1990.

Schón, G and Simon, U., A Fascinating New Field in Colloid Science: Small Ligand–stabilized Metal Clusters and their Possible Application in Microelectronics, *Colloid Polym. Sci.*, 273:202–218, 1995.

Seeman, N., DNA Components for Molecular Architecture, *Accounts of Chemical Research*, 30:357–363, 1997.

Simon, U., et al., The Application of $Au_{55}$ Clusters as Quantum Dots, *Angew Chem. Int. Ed. Engl*, 32:250–254, 1993.

Whitesell, J., et al., Directionally Aligned Helical Peptides on Surfaces, *Science*, 261:73–76, 1993.

Wybourne, M., et al., Coulomb–blockade Dominated Transport in Patterned Gold–Cluster Structures, *Jpn. J. Appl. Phys.*, 36:7796–7800, 1997.

Yano, K., et al., Transport Characteristics of Polycrystalline–Silicon Wire Influenced by Single–Electron Charging at Room Temperature, *Appl. Phys. Lett.*, 67:828–830, 1995.

Abstract of poster entitled: "Synthesis of subnanometer water–soluble thiol–stabilized nanoparticles by ligand exchange reactions." Gerd Woehrle, Marvin Warner, and James Hutchison, published on the Web circa Jun. 14, 2001.

Bartlett, P.A., et al., "Synthesis of Water–Soluble Undecagold Cluster Compounds of Potential Importance in Electron Microscopic and Other Studies of Biological Systems," *J. Am. Chem. Soc.*, vol. 100, pp. 5085–5089 (1978).

Mao, C., et al., "Designed Two–Dimensional DNA Holliday Junction Arrays Visualized by Atomic Force Microscopy," *J. Am. Chem. Soc.*, vol. 121, p. 5437–5443 (1999).

Storhoff, J.J. et al., "Programmed Materials Synthesis with DNA," *Chem. Rev.*, vol. 99, pp. 1849–1862 (1999).

Winfree, E., et al., "Design and Self–Assembly of Two–Dimensional DNA Crystals," *Nature*, vol. 394, pp. 539–544 (1998).

Woehrle, G., et al., "Ligand Exchange Reactions Yield Subnanometer, Thiol–Stabilized Gold Particles with Defined Optical Transitions," *J. Phys. Chem. B*, vol. 106, pp. 9979–9981 (2002).

International Search Report for International Application No. PCT/US03/20500, *International Searching Authority*, Dec. 11, 2003.

* cited by examiner

SCAFFOLD-ORGANIZED CLUSTERS AND ELECTRONIC MADE USING SUCH CLUSTERS

CROSS REFERENCE TO RELATED APPLICATION

This application is a divisional application of U.S. application Ser. No. 09/817,708, filed Mar. 26, 2001, now U.S. Pat. No. 6,730,537 which claims priority from prior U.S. provisional applications, Nos. 60/191,814, filed Mar. 24, 2000, entitled Scaffold-Organized Metal, Alloy, Semiconductor and/or Magnetic Clusters and Electronic Devices Made Using Such Clusters; 60/226,720, filed on Aug. 21, 2000, entitled Scaffold Organized Clusters; and 60/231,193, filed Sep. 7, 2000, entitled Scaffold Organized Clusters. These prior applications are incorporated herein by reference.

STATEMENT OF GOVERNMENT RIGHTS

This invention was made with government support under contract numbers N00014-93-0618 and N00014-93-1-1120 awarded by the Department of Defense, Office of Naval Research, and under Grant No. DMR-9705343 awarded by the National Science Foundation. The government has certain rights in the invention.

FIELD

This invention concerns a method for forming organized arrays of metal, alloy, semiconductor and/or magnetic clusters for use in the manufacture of electronic devices, such as high-density memory storage and nanoelectronic devices.

BACKGROUND

Fundamentally new technologies are required to continue increasing device integration density and speed. Conventional metal-oxide semiconductor-field-effect transistors soon will reach fundamental density and speed limits as a result of quantum mechanical tunneling. In order to scale electronic device sizes down to nanometer dimensions, systems containing increasingly fewer numbers of particles must be considered.

The ultimate limit is a system in which the transfer of a single charge quanta corresponds to information transfer or some type of logic operation. Such single-electron systems are presently the focus of intense research activity. See, for example, *Single Charge Tunneling, Coulomb Blockade Phenomena in Nanostructure*, edited by H. Grabert and M. H. Devoret, NATO ASI Series B: Physics Vol. 294 (1992). These systems have potential application to nanoelectronic circuits that have integration densities far exceeding those of present day semiconductor technology. See, *Quantum Transport in Ultrasmall Devices*, edited by D. K. Ferry, H. L. Grubin, C. Jacoboni, and A. Jauho, NATO ASI Series B: Physics Vol. 342 (1995).

Single-electron transistors based on the concept of Coulomb blockade are one proposed technology for realizing ultra-dense circuits. K. K. Likharev, *Single-electron Transistors: Electrostatic Analogs of the DC SQUIDS,"* IEEE Trans. Magn. 23:1142 (1987); and *IBM J. Res. Dev.* 32:144 (1988). Coulomb blockade is the suppression of single-electron tunneling into metallic or semiconductor islands. In order to achieve Coulomb blockade, the charging energy of an island must greatly exceed the thermal energy. To reduce quantum fluctuations the tunneling resistance to the island should be greater than the resistance quantum $h/e^2$. Coulomb blockade itself may be the basis of conventional logic elements, such as inverters. Id.

Equally promising is the fact that the Coulomb blockade effect can be used to pump charges one-by-one through a chain of dots to realize a frequency-controlled current source in which the current is exactly equal to I=ef, where f is the clocking frequency. See, L. J. Geerligs et al., *Frequency-locked Turnstile Device for Single-electrons*, Phys. Rev. Lett., 64:2691 (1990); and H. Pothier et al., *Single-Electron Pump Based on Charging Effects*, Europhys. Lett. 17:249 (1992). Such turnstile devices are of fundamental interest as highly accurate current standards.

The clocking of charge through an array is also one model of information storage. It is possible that computation may be based on switching of currents rather than charge which, due to the extreme accuracy of single-electron current sources, may be more robust towards unwanted fluctuations than single-electron transistor-based circuits.

One of the most promising technologies for realizing terabyte memories is founded on the principle of the Coulomb blockade. Yano et al. have demonstrated room temperature operation of single-electron devices based on silicon nanocrystals embedded in $SiO_2$. K. Yano et al., *Room-Temperature Single-electron Memory, IEEE Trans. Electron. Devices*, 41:1628 (1994); and K. Yano et al., *Transport Characteristics of Polycrystalline-Silicon Wire Influenced by Single-electron Charging at Room Temperature, Appl. Phys. Lett.*, 67:828 (1995). Recently, a fully integrated 8×8 memory array using this technology has been reported. K. Yano et al., *Single-Electron-Memory Integrated Circuit for Giga-to-Tera Bit Storage, IEEE International Solid State Circuits Conference*, p. 266–267 (1996).

Microelectronic devices based on the principle of Coulomb blockade have been proposed as a new approach to realizing electronic circuits or memory densities that go beyond the predicted scaling limit for present day semiconductor technology. While the operation of Coulomb blockade devices has been demonstrated, most operate only at greatly reduced temperatures and require sophisticated nanofabrication procedures. The size scales necessary for Coulomb blockade effects at such relatively elevated temperatures of about room temperature impose limits on the number, uniformity and connectivity of quantum dots. As a result, alternative methodologies of nanofabrication need to be investigated and developed.

SUMMARY

The present invention provides a new process for making arrays comprising metal, alloy, semiconductor and/or magnetic clusters. An "array" can be any arrangement of plural such clusters that is useful for forming electronic devices. Three primary examples of uses for such arrays are (1) electronic circuits, (2) arrangements of computer memory elements, both of which can be in one or several planes, and (3) sensors.

"Clusters" as used herein refers to more than one, and typically three or more, metal, alloy, semiconductor or magnetic atoms coupled to one another by metal-type bonds or ionic bonds. Clusters are intermediate in size between single atoms and colloidal materials. Clusters made in accordance with the present invention also are referred to herein as "nanoparticles." This indicates that the radius of each such cluster is on the order of about one nanometer. A primary goal of the present invention is to provide electronic devices that operate at or about room temperature. This is possible if the cluster size is made small enough to meet Coulomb blockade charging energy requirements at room temperature. While cluster size itself is not dispositive of whether the clusters are useful for forming devices operable at or about room temperature, cluster size is nonetheless quite important. It currently is believed that clusters having radii much larger than about two nanometers likely will not be useful for forming electronic devices that operate at or about room temperature.

The metal, alloy, semiconductor and/or magnetic clusters are bonded to "scaffolds" to organize the clusters into arrays. "Scaffolds" are any molecules, including polymers, that can be placed on a substrate in predetermined patterns, such as linear bridges between electrodes, and to which clusters can be bonded to provide organized cluster arrays. Without limitation, scaffolds include biomolecules, such as polynucleotides, polypeptides, and mixtures thereof. Polypeptides capable of forming α-helices are particularly useful scaffold-forming molecules. Polypeptides that are capable of forming other secondary structures, such as $3_{10}$-helices, π-helices, and β-sheets may in certain embodiments serve as scaffolds. Polypeptides that are capable of forming repetitive higher order structures (i.e., tertiary, and quaternary structures) may also serve as scaffolds. One example is the collagen helix. Double stranded DNA, Holliday junctions, and RNA hairpins are non-limiting examples of polynucleotide scaffolds.

One embodiment of a method for forming arrays of metal, alloy, semiconductor and/or magnetic clusters involves placing a scaffold on a substrate, in, for example, a predetermined pattern. Arrays are formed by contacting the scaffold with plural, monodispersed (clusters of substantially the same size) ligand-stabilized metal, alloy, semiconductor and/or magnetic clusters that couple to the scaffold. If the clusters are metal clusters, then the metal may be selected from the group consisting of Ag, Au, Pt, Pd and mixtures thereof. If gold is the metal, the metal cluster may be $Au_{55}$.

Clusters may be coupled to a scaffold by ligand exchange reactions. Each cluster, prior to contacting the scaffold, includes plural exchangeable ligands bonded thereto. The ligand-exchange reactions involve exchanging functional groups of the scaffold for at least one of the exchangeable ligands of the cluster that is present prior to contacting the scaffold with the clusters. Examples of exchangeable ligands suitable for forming metal clusters in accordance with the invention may be selected from the group consisting of thiols, thioethers (i.e., sulfides), thioesters, disulfides, sulfur-containing heterocycles, 1°, 2° and perhaps 3° amines, pyridines, phosphines, carboxylates, nitriles, hydroxyl-bearing compounds, such as alcohols, and mixtures thereof. Thiols are particularly useful ligands for practicing the present invention.

Clusters may also be coupled to the scaffold by electrostatic interactions between the cluster and the scaffold. For example, clusters may include plural ligands that possess a charge or charges, either positive or negative, that serve to attract the clusters to oppositely charged scaffolds. In one embodiment, the cluster includes ligands having at least one positive charge and the scaffold is a polynucleotide having plural negative charges along its phosphate backbone. In a more particular embodiment, the cluster includes ligands having quaternary ammonium groups. In another embodiment, the cluster includes ligands with at least one negative charge, such as ligands having carboxylate or sulfonate group(s), and the scaffold is a polypeptide, such as polylysine (PL), having plural positive charges. In a particular disclosed embodiment, the scaffold is poly-L-lysine (PLL).

Clusters may be coupled to a scaffold through hydrophobic interactions. In one embodiment, the cluster includes ligands with a portion that can intercalate into DNA. For example the portion may be an anthraquinone. Other examples of suitable intercalating portions include planar cations such as acridine orange, ethidium, and proflavin. In some embodiments, the portion facilitates intercalation at particular, sequence-specific sites within a DNA molecule. In other embodiments the clusters are coupled to a scaffold through covalent bonds between the ligands of the cluster and the scaffold.

There are several methods for placing a scaffold onto a substrate in predetermined patterns. For example, one method comprises aligning scaffold molecules in an electric field created between electrodes on the substrate. It therefore will be appreciated that the scaffold molecules advantageously have a dipole moment sufficient to allow them to align between the electrodes. This is one reason why polypeptides that form α helices are particularly useful. The α-helix structure imparts a sufficient dipole to the polypeptide molecules to allow alignment of the molecules between the electrodes upon formation of an electrical field. One example of a polypeptide useful for forming scaffolds in accordance with the present invention is polylysine. Similarly, polynucleotides, such as DNA, that assume helical structures may be aligned by electric fields.

Another method of patterning scaffold molecules comprises polymerizing monomers, oligomers (10 amino acids or nucleotides or less), or small polynucleotides or polypeptides into longer molecules on the surface of a substrate. For example, scaffold molecules can be polymerized as a bridge between electrodes on a substrate.

Yet another method of placing a scaffold onto a substrate in a predetermined pattern is by anchoring the scaffold and inducing alignment of the anchored scaffold in a particular direction by fluid flow. For example, a scaffold may be aligned between two electrodes by attaching the scaffold to a first electrode and using fluid flow in the direction of a second electrode to align the scaffold with the direction between the two electrodes. In a particular embodiment, the substrate is mica, the scaffold is DNA, and the DNA is attached to the first electrode using a thiol linkage. Fluid-induced alignment is used to align the scaffold in the direction of the second electrode, and the DNA scaffold is bound to the mica substrate by $Mg^{2+}$ ions, thereby holding the DNA in its aligned position. Fluid-induced alignment may also be subsequently used to align additional scaffolds so that they cross, or intersect scaffolds already aligned on the substrate.

Other methods of placing a scaffold onto a substrate in a predetermined pattern include positioning the scaffold on a substrate using magnetic fields, optical tweezers, or laser traps. Multiple scaffolds may be arranged on a substrate using any of the above methods. Scaffolds may not only be aligned between electrodes but may also be aligned such that they cross or otherwise contact each other to form one-, two- or three-dimensional structures useful as templates for forming electronic devices comprising cluster arrays. Such cluster arrays may be used to provide high density electronic or memory devices that operate on the principle of Coulomb blockade at ambient temperatures.

The present invention also provides compositions that are useful, for example, for forming metal, alloy, semiconductor and/or magnetic cluster arrays. In a particular embodiment, the composition comprises monodispersed, ligand-stabilized $Au_{55}$ metal clusters coupled to a polypeptide in the shape of or capable of forming an α-helix with the metal clusters bonded thereto. In another embodiment, the composition comprises monodispersed, ligand stabilized gold metal clusters coupled to a polynucleotide capable of forming a helical structure. In particular embodiments, the metal clusters have metal-cluster radii of from about 0.4 nm to about 1.8 nm, such as from about 0.4 nm to about 1.0 nm.

In particular embodiments, the present invention includes compositions comprising a polypeptide capable of forming α-helix and plural monodispersed, ligand-stabilized metal and/or semiconductor clusters, each cluster having plural ligands that serve to couple the clusters to the polypeptide. In more particular embodiments, the plural ligands of the clusters interact with the polypeptide by an interaction selected from the group consisting of ligand exchange reactions, electrostatic interactions, hydrophobic interaction, and combinations thereof. In other more particular embodiments, the metal and/or semiconductor clusters have radii of from about 0.4 nm to about 1.8 nm, such as between about 0.4 nm and about 1.0 nm. If the clusters comprise metal clusters the metal may be selected from the group consisting of Au, Ag, Pt, Pd and mixtures thereof, and in particular embodiments the clusters may comprise $Au_{55}$ metal clusters.

Compositions comprising polynucleotides capable of forming helical structures and plural monodispersed, ligand-stabilized metal and/or semiconductor clusters, where each cluster having plural ligands serves to couple the clusters to the polynucleotide are also provided by the invention. The plural ligands of the clusters may serve to interact and couple the cluster to the polynucleotide through interactions such as ligand exchange reactions, electrostatic interactions, hydrophobic interactions, intercalation reactions and combinations thereof.

In particular embodiments the invention provides organized arrays of metal clusters comprising monodispersed, ligand-stabilized metal clusters having metal-cluster radii of from about 0.4 nm to about 1.8 nm, the metal being selected from the group consisting of Ag, Au, Pt, Pd and mixtures thereof. Such arrays include a scaffold and the metal clusters are coupled to the scaffold to form the organized array.

The present invention further provides an electronic device that operates at or about room temperature based on the Coulomb blockade effect. Such electronic devices include a first cluster (e.g. a cluster comprising a metal cluster core having a radius of between about 0.4 nm and about 1.8 nm) and a second such cluster. The clusters are physically spaced apart from each other at a distance of less than about 5 nm by coupling the clusters to a scaffold, such as a biomolecular scaffold, so that the physical separation between the clusters is maintained. Electronic devices according to the invention may also include pairs of biomolecular scaffolds, each with coupled clusters, arranged so that the scaffolds intersect to provide electric circuit elements, such as single-electron transistors and electron turnstiles. Such elements may be useful as components of chemical sensors or ultrasensitive electrometers. Because of their unique architecture, electronic devices according to the invention exhibit a linear increase in the number of electrons passing between pairs of clusters as the potential difference between the two clusters is increased above a threshold value.

The present invention also provides methods of forming monodispersed phosphine-stabilized gold nanoparticles that allow the radii of nanoparticles to be controllably adjusted. In one embodiment, the method comprises dissolving $HAuCl_4$ and $PPh_3$ in a biphasic system (for example, a biphasic system comprising a water phase, an organic phase, and a phase transfer catalyst) and adding sodium borohydride to the biphasic system. In particular embodiments, the biphasic system may comprise water and an organic solvent selected from the group consisting of toluene, xylenes, benzene, and mixtures thereof. The phase transfer catalyst may be a quaternary ammonium salt, for example, tetraoctylammonium bromide. Control of the nanoparticle size may be accomplished through control of the rate at which sodium borohydride is added to the biphasic system.

The invention also provides methods of preparing thiol-stabilized gold nanoparticles. Thiol-stabilized gold nanoparticles may be prepared by dissolving phosphine-stabilized gold nanoparticles in an organic solvent and exchanging the phosphine ligands of the phosphine-stabilized gold nanoparticle for thiol ligands. Particles that are particularly useful for preparing arrays according to the invention are prepared from thiol ligands that comprise a group or groups of atoms that are capable of coupling thiol-stabilized gold nanoparticle to scaffolds. Phosphine and thiol ligands may be prepared in a single-phase system if the thiol ligand is soluble in an organic solvent. However, if the thiol ligand(s) is water soluble, it is still possible to exchange thiol ligands for phosphine ligands at the interface between a water-immiscible organic solvent containing the phosphine stabilized gold nanoparticles and water containing the thiol ligand(s).

DETAILED DESCRIPTION

Abbreviations and Definitions

Figure 1:
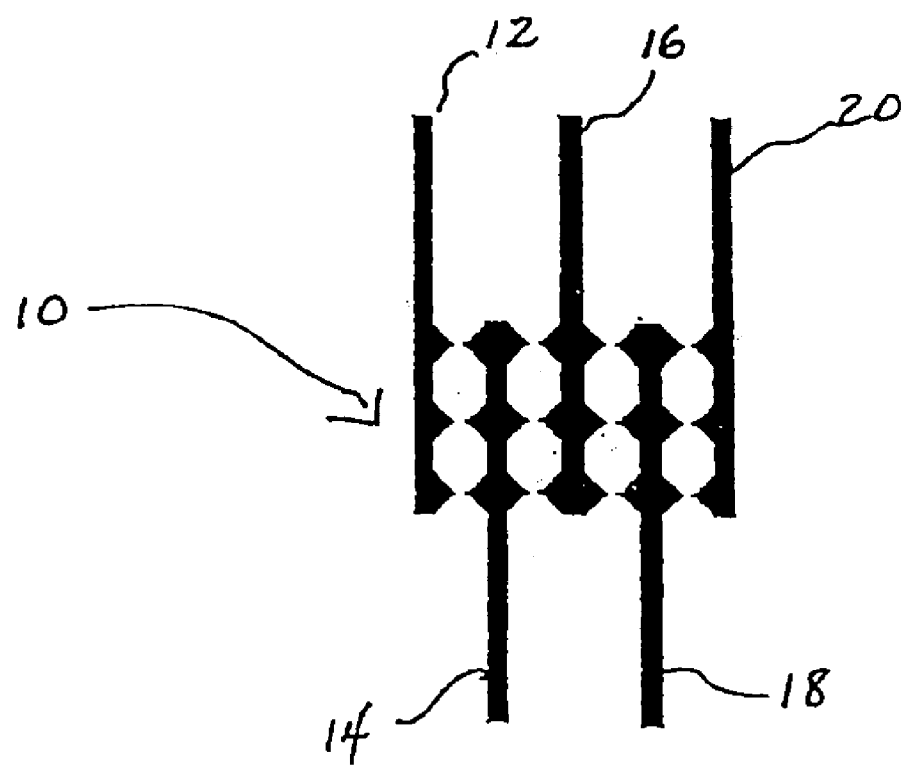
FIG. 1 is a schematic diagram of an interdigitated electrode array having saw-tooth edges.

The singular forms "a," "an," and "the" refer to one or more unless the context clearly indicates otherwise.

PL—polylysine
PLL—poly-L-lysine
AFM—atomic force microscopy
TEM—transmission electron microscopy
SEM—scanning electron microscopy
XPS—x-ray photoelectron spectroscopy
ODT—octadecylthiol
TOABr—tetraoctylammonium bromide
$Au_{55}$—refers to gold nanoparticles prepared by the Schmid preparation, having a diameter of approximately 1.4 nm.

The general steps used to produce organized arrays comprising metal, alloy, semiconductor and/or magnetic clusters in accordance with the present invention include (1) attaching molecular scaffolds to substrates in predetermined patterns, (2) forming monodispersed, relatively small (i.e., nanoparticle size, with room temperature Coulomb blockade applications typically using nanoparticles where the diameter of the core, $d_{core}$ is less than about 2 nm) ligand-stabilized metal, alloy, semiconductor and/or magnetic clusters, (3) coupling the ligand-stabilized clusters to the scaffolds to form organized arrays, (4) coupling electrical contacts to the organized arrays, and (5) using such constructs to form electronic, particularly nanoelectronic, devices. The substrate generally is a metal, glass or semiconductor material.

Most efforts have been directed to developing working devices using metal clusters. Certain of the following passages therefore focus on describing how to make and use devices based on metal cluster arrays. It should be understood, however, that any reference in this application to "metal clusters" or "clusters" typically also refers to alloy clusters, semiconductor clusters, magnetic clusters, and combinations thereof.

Important features of the present invention include the small physical size of the metal clusters, the ligand exchange chemistry and the nature of the ligand shell produced by the ligand exchange chemistry. The small physical size of the metal clusters provides a large Coulomb charging energy. The ligand-exchange chemistry provides a means to tailor the ligand shell for a particular purpose and immobilize the clusters on biomolecules. And, the ligand shell offers a uniform and chemically adjustable tunnel barrier between cluster cores.

The following paragraphs describe the present invention in greater detail.

I. Forming Monodispersed Ligand-Stabilized Clusters

A feature of the present invention is the recognition that monodispersed, relatively small metal clusters can be used to develop electronic devices that operate at or about room temperature based on the Coulomb blockade effect. "Monodispersed" refers to the formation of a population of metal clusters of substantially the same size, i.e., having substantially the same radii (or diameters). In contrast, prior-art approaches typically have used polydispersed metal clusters where the size of the metal clusters is not substantially uniform. A completely monodispersed population is one in which the size of the metal clusters is identical. However, complete monodispersity is difficult, if not impossible, to achieve. And complete monodispersity is not required to produce devices operating at room temperature based on the Coulomb blockade effect. Nevertheless, as the dispersity of the cluster population proceeds from absolute monodispersity towards polydispersity the likelihood that the device will operate reliably at room temperature based on the Coulomb blockade effect decreases.

Moreover, as the radius of the metal cluster decreases, the intrinsic capacitance gets smaller. As capacitance gets smaller, the charging energy of the cluster gets larger. Coulomb blockade effects are observed when the charging energy exceeds the thermal energy at room temperature. Prior approaches have used clusters having radii generally larger than would be useful for forming devices that operate at room temperature based on the Coulomb blockade effect. In contrast, the present invention forms metal "nanoparticles" having relatively small radii. The size requirement for clusters made in accordance with the present invention can be established in at least two ways, (1) by stating absolute radius lengths, and (2) by comparing the radius of the cluster in question to the radius of gold clusters having magic numbers (see the discussion provided below) of gold atoms.

In terms of absolute numbers, "nanoparticle" is defined herein as a cluster having a radius of from about 0.4 nm to about 1.8 nm (4 Å to about 18 Å), for example, from about 0.4 nm to about 1.25 nm (4 Å to about 12.5 Å), such as from about 0.4 nm to about 1.0 nm (4 Å to about 10 Å). These radius lengths refer solely to the radius of the metal cluster, and not the radius of the metal cluster and ligand sphere.

With its insulating ligand shell, the diameter of the ligand-stabilized metal cluster can vary. The size of the ligand shell may influence the electron tunneling rate between clusters. Tunneling rate is exponentially related to the thickness of the ligand shell. As a result, the diameter of the ligand shell may be tailored for a particular purpose. It currently is believed that the diameters for ligand-stabilized clusters useful for practicing the present invention should be from about 2.5 nm to about 5 nm. The relatively large metal clusters made previously do not provide a large Coulomb charging energy and do not operate at room temperature, and instead generally only operate at temperatures of from about 50 mK to about 10K.

"Bare" clusters, i.e., those without ligand shells, also may be useful for practicing the present invention. For example, bare clusters can be used to form electrical contacts.

Still another consideration is the distance between the edges of metal cluster cores. It currently is believed that the maximum distance between the edges of cluster cores for clusters useful for practicing the present invention is about 5 nm (50 Å), and ideally is on the order of from about 1 to about 2 nm (10–20 Å Å).

Originally it was believed that clusters in accordance with the present invention generally should include numbers of atoms that are based on the so-called "geometric magic numbers" of atoms surrounded by a ligand shell. Geometric magic numbers result from the most densely packed arrangement of atoms that form a "sphere." Magic numbers are given by Formula 1 below $$1 + \sum_{n=1}^{k}(10n^2 + 2) \quad \text{Formula 1}$$

where k is an integer that represents the number of shells of metal atoms surrounding a central atom. Noble metal clusters with k=2, 4, 6, 7 and 8 have been synthesized and stabilized by a ligand shell. While clusters having magic numbers of atoms will work to practice the present invention, it has now been determined that magic numbers of atoms likely are not required to provide clusters useful for practicing the present invention.

Solely by way of example, metals used to form ligand-stabilized metal clusters in accordance with the present invention may be selected from the group consisting of silver (Ag), gold (Au), platinum (Pt), palladium (Pd), and mixtures thereof. "Mixtures thereof" refers to having more than one type of metal cluster coupled to a particular scaffold, or different metal clusters bonded to different scaffolds used to form a particular electronic device. It also is possible that metal alloy clusters, e.g., gold/palladium clusters, can be used to form cluster arrays and electronic devices in accordance with the present invention.

Gold is a particularly useful metal for forming ligand-stabilized monodispersed metal clusters. This is because (1) the ligand exchange chemistry for gold nanoparticles and the nature of the ligand shell formed about gold is well understood, (2) $Au_{55}$ has a diameter of about 1.4 nm, which is particularly useful for forming organized metal arrays that exhibit the Coulomb blockade effect at or about room temperature, and (3) it is possible to prepare nearly mono-dispersed gold clusters without lengthy purification requirements, such as lengthy crystallization processes.

Assuming that magic numbers do provide benefit, the magic numbers of gold, palladium and platinum atoms for use with the present invention are 13, 55, 147 and 309. The magic number 55 is a particularly suitable magic number (represented as $Au_{55}$, $Pd_{55}$ and $Pt_{55}$). The magic number of silver atoms for silver metal clusters useful for practicing the present invention may be the same as for gold.

Semiconductor materials may also be useful for practicing the present invention. Semiconductor materials that may be prepared as nanoparticles and stabilized with ligand spheres include, without limitation, cadmium selenide, zinc selenide, cadmium sulfide, cadmium telluride, cadmium-mercury-telluride, zinc telluride, gallium arsenide, indium arsenide and lead sulfide.

Magnetic particles also may be used to decorate scaffolds in accordance with the present invention. An example, without limitation, of such magnetic particles is iron oxide ($Fe_2O_3$).

II. Ligands

A. Background

Once a suitable metal, alloy, semiconductor and/or magnetic material is selected for forming nanoparticles, ligands for bonding to the clusters also must be selected. The assembly of clusters into Coulomb blockade structures requires molecular-scale organization of the clusters while simultaneously maintaining the insulating ligand sphere between individual clusters. The clusters also should be coupled to the scaffold in a sufficiently robust manner to allow for fabrication of devices incorporating cluster arrays.

This may be accomplished by ligand exchange reactions. The selection of ligands for forming an insulating ligand layer about the cluster and for undergoing ligand exchange reactions therefore is a consideration. Criteria useful for selecting appropriate ligands include, but are not limited to, (1) the ligands are capable of coupling with the scaffold, such as through ligand-exchange, acid-base or intercalation reactions (2) the ligands increase the solubility of the ligand-metal cluster complexes in organic solvents, thereby facilitating synthesis of metal clusters and subsequent reactions, and (3) the ligands form well ordered metal-ligand complexes having diameters that promote room temperature Coulomb-blockade effects.

B. Classes of Ligands

Ligands suitable for forming metal clusters in accordance with the present invention may be selected, without limitation, from the group consisting of: thiols (RSH); thioethers (also known as sulfides, R—S—R'); thioesters (RCOSR); disulfides (R—S—S—R'); sulfur-containing heterocycles, such as thiophene; 1°, 2° and 3° amines ($RNH_2$, $R_2NH$ and $R_3N$, respectively), particularly 1° amines; pyridines; phosphines ($R_3P$); carboxylates ($RCO_2$—); nitriles (RCN); hydroxyl-bearing compounds, such as alcohols (ROH); and mixtures thereof. Additional guidance concerning the selection of ligands can be obtained from Michael Natan et al.'s *Preparation and Characterization of Au Colloid Monolayers, Anal. Chem.*, 67:735–743 (1995), which is incorporated herein by reference.

Organic sulfur-containing molecules (e.g., thiols, thioethers, thioesters, disulfides, sulfur-containing heterocycles, and mixtures thereof) are particularly useful class of ligands. Thiols, for example, are a suitable type of sulfur-containing ligand for several reasons. Thiols have an affinity for gold, which may be formed into electrodes or electrode patterns. Moreover, thiols have been shown to be good ligands for stabilizing gold clusters. And, many thiol-based ligands are commercially available. The thiols form ligand-stabilized metal clusters having a formula $M_x(SR)_n$ wherein M is a metal, R is an alkyl chain or aromatic group, x is a number of metal atoms that provide metal clusters having the characteristics described above, and n is the number of thiol ligands attached to the ligand-stabilized metal clusters.

C. Organic Portion of Ligands

The organic portion of ligands useful for practicing the present invention also can vary. For example, the length of the alkyl chain can be varied to obtain particular features desired in the ligand-stabilized metal clusters. These include the solubility of the metal clusters in solvents used to carry out the present invention, and the size and insulating characteristics of the ligand-stabilized metal clusters. Alkyl chains having from about 2 carbon atoms to about 20 carbon atoms are particularly suitable for practicing the present invention.

Aryl-type ligands, i.e., aromatic groups such as phenyl rings, containing or having sulfur atoms coupled thereto also may serve as ligands for forming ligand-stabilized metal clusters. For example, mercaptobiphenyl (HS-phenyl-phenyl) has been used to form ligand-stabilized gold clusters. The aromatic rings of such compounds may further include functional groups capable of reacting with the scaffold molecules. For example, the aromatic rings may include acidic groups, such as carboxylic acids, for acid-base reactions with functional groups of the scaffold molecules, such as amines.

Aromatic ligands are quite useful for producing rigid arrays, thereby stabilizing the electron transport properties.

For this reason, aryl ligands currently are particularly useful ligands for practicing the present invention. In addition, small alkyl groups, such as thioproprionic acid, also provide rigid ligand systems.

Ligands that intercalate into DNA also may be used, since this provides a convenient means for attaching clusters to DNA molecules. Typically, the DNA intercalating ligands include rigid n systems. Examples of such DNA intercalating ligands include, without limitation, anthraquinone, phenanthridinium, acridine orange, proflavin, ethidium, combinations thereof and derivatives thereof. DNA intercalating ligands may also be DNA-sequence dependent. Thus, DNA having particular sequences can be used as a scaffold that is intercalated at predetermined portions of the scaffold. This provides a method for controlling and altering the spacing between metal clusters.

The ligands also can be inter-and/or intra-molecularly crosslinked. For example, intercalating ligands may be photo-crosslinked to the scaffold to provide more rigid systems.

Based on these considerations, a diverse family of functionalized nanoparticles has been prepared using a 1.4 nm core metal cluster [CORE]. Ligand exchange has used to prepare, from $Au_{55}[P(C_6H_5)_3]_{12}Cl_6$, a wide variety of ligand stabilized clusters of the general formulas $CORE-[PX_3]_n$, $CORE-[S-X]_n$, and $CORE-[NHX]_n$ where X serves to couple the cluster to a scaffold and n is at least one. For example, X may include groups of atoms capable of acid-base reactions with scaffolds, groups of atoms capable of hydrophobic interactions with scaffolds, groups of atoms capable of intercalating in nucleic acids (e.g. DNA), groups of atoms capable of hydrogen bonding to scaffolds, groups capable of electrostatic interactions with scaffolds, and groups capable of forming covalent bonds with a scaffold. Groups of atoms that facilitate interaction with scaffolds include, without limitation, alkyl groups from about $C_3$ to $C_{18}$, aryl groups, carboxylic acid groups, sulfonic acid groups, peptide groups, amine groups, and ammonium groups. Other functional groups that may be part of X include aldehyde groups and amide groups.

Charged species are especially useful for electrostatic coupling of clusters to oppositely charged scaffolds. For example, ligands having positively charged quaternary ammonium groups have been made that interact strongly with anionic scaffolds, such as phosphate backbone of DNA. Ligands having negatively charged sulfonate groups have been made for interacting with positively charged scaffolds, such as poly-L-lysine.

Specific examples of functionalized nanoparticles include: phosphine-based clusters of the formula $CORE-(PR_3)_n$, where the R groups are independently selected from the group consisting of phenyl, cyclohexyl and alkane, for example, octyl, and n is at least one; amine-based clusters of the formula $CORE-(NHR)_n$, where R is selected from alkyl groups having 20 or fewer carbon atoms, for example, pentadecyl and n is at least one; and thiol-based clusters of the formula $CORE-(SR)_n$ where the R group is selected from the group consisting of phenyl, biphenyl, alkyl groups having 20 or fewer carbon atoms, for example, propyl, hexyl, nonyl, undecyl, hexadecyl and octadecyl, and n is at least one. Yet other examples include clusters of the formula $CORE-[S-(CH_2)_xCOOH]_n$, where x is between about 2 and about 19 and n is at least one, for example, where x is equal to 2, 5, or 10; clusters of the formula $CORE-[S-(CH_2)_xOH]_n$ where x is between about 2 and about 20 and n is at least one, for example, where x is equal to 2; clusters of the formula $CORE-[S-(CH_2)_xNR_2]_n$ where R is independently selected from the group consisting of hydrogen and C1–C4 alkyl, x is between about 2 and about 20 and n is at least one, for example, where x=2 and R is methyl; clusters of the formula $CORE-[S-(CH_2)_xNR_3^+]_n$ where R is independently selected from the group consisting of C1–C4 alkyl, x is between about 2 and about 20, and n is at least one, for example, where x=2, and R is methyl; clusters of the formula $CORE-[S-(CH_2)_xSO_3^-]_n$ where x is between about 2 and about 20, and n is at least one, for example, where x=2; clusters of the formula $CORE-[S-(CH_2)_xCONH(CH_2)_yCH_3]_n$ where x+y is between 1 and about 20 and n is at least one, for example, where x=2 and y=14; clusters with amino-acid containing ligands, including glycine-based ligands, such as $CORE-[-S-(CH_2)_2COGlyGlyOH]_n$, and clusters having intercalating ligands, such as shown below.

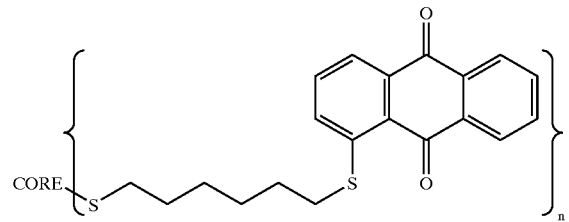

D. General Method for Producing Ligand-Stabilized Metal Clusters

The general approach to making ligand-stabilized metal clusters first comprises forming monodispersed metal clusters having displaceable ligands. This can be accomplished by directly forming monodispersed metal clusters having the appropriate ligands attached thereto, but is more likely accomplished by first forming monodispersed, ligand-stabilized metal clusters which act as precursors for subsequent ligand-exchange reactions with ligands that are more useful for coupling clusters to scaffolds.

One example, without limitation, of a monodispersed gold cluster that has been produced and which is useful for subsequent ligand-exchange reactions with the ligands listed above is $Au_{55}[P(C_6H_5)_3]_{12}Cl_6$. A procedure for making monodispersed $Au_{55}[P(C_6H_5)_3]_{12}Cl_6$ nanoparticles is provided by G. Schmid, *Hexachlorodecakis (triphenylphosphine)-pentapentacontagold*, $Au_{55}[P(C_6H_5)_3]_{12}Cl_6$, *Inorg. Syn.*, 27:214–218 (1990). Schmid's publication is incorporated herein by reference. Schmid's synthesis involves the reduction of $AuCl[PPh_3]$. Example 1 below also discusses the synthesis of $Au_{55}[P(C_6H_5)_3]_{12}Cl_6$. One advantage or Schmid's synthesis is the relatively small size distribution of clusters produced by the method, e.g., 1.4±0.4 nm.

Once ligand-stabilized monodispersed metal clusters are obtained, such clusters can be used for subsequent ligand-exchange reactions, as long as the ligand-exchange reaction is readily facile and produces monodispersed metal clusters. Prior to the present invention it was not appreciated that the $Au_{55}[P(C_6H_5)_3]_{12}C_{16}$ clusters could be used to form nearly monodispersed derivatives by ligand-exchange chemistry. In fact, some literature reports indicated that it was difficult, if not impossible, to form linked metal clusters by ligand-exchange reactions. See, for example, Andres et al.'s *Self-Assembly of a Two-Dimensional Supperlattice of Molecularly Linked Metal Clusters*, Science, 273:1690–1693 (1996).

To perform ligand-exchange reactions, a reaction mixture is formed comprising the metal cluster having exchangeable ligands attached thereto and the ligands to be attached to the metal cluster, such as thiols. A precipitate generally forms upon solvent removal, and this precipitate is then isolated by conventional techniques. See Examples 2 and 3 for further details concerning the synthesis of ligand-stabilized metals.

III. Molecular Scaffolds

A. Background

Metal clusters produced as stated above are coupled to molecular scaffolds. "Coupling" as used herein refers to some interaction between the scaffold and the ligand-stabilized metal clusters such that the metal clusters become associated with the scaffold. Associated may mean covalently bound, but also can include other molecular associations, such as electrostatic interactions (including dipole-dipole interactions, charge-dipole interactions, and charge-charge interactions), and hydrophobic interactions. "Coupling" includes attaching clusters to scaffolds by (1) ligand exchange reactions where functional groups of the scaffold molecules, such as sulfur-containing functional groups or amines, exchange with the ligands of the metal-ligand cluster, (2) acid-base type reactions between the ligands and molecules of the scaffold, (3) intercalation of a ligand into a nucleic acid (e.g., DNA) helix, and (4) electrostatic interactions between charged clusters and oppositely charged scaffolds.

B. Scaffolds Comprising Biomolecules

To form useful electronic devices, the scaffolds are advantageously disposed on a substrate in predetermined patterns to which electric contacts can be made. The scaffolds of the present invention may comprise biomolecules, such as polynucleotides, polypeptides and mixtures thereof, and hence may be referred to as biomolecular scaffolds. There is some precedent for using polynucleotides for forming molecular scaffolds. See, for example, C. A. Mirkin et al., *A DNA-Based Method for Rationally Assembling Nanoparticles into Macroscopic Materials*, Nature, 382:607 (1996); and A. P. Alivisatos et al., *Organization of "Nanocrystal Molecules" using DNA*, Nature, 382:609 (1996). Each of these references is incorporated herein by reference. Polynucleotides provide a different spacing between metal clusters than do polypeptides. Thus, spacing between metal clusters can be varied by changing the nature of the scaffold.

Polypeptides include polypeptides that form α-helical secondary structures. Certain peptides, although attractive candidates from the standpoint of being stabilizing ligands for the metal clusters, do not form α-helices. However, many polypeptides do form α-helices, and hence are good candidates for forming scaffolds in accordance with the present invention.

It also should be appreciated that the polypeptide can be a "homopolypeptide," defined herein to refer to polypeptides having only one type of amino acid. One example of a homopolypeptide is polylysine. The free base form of polylysine readily forms an α-helix. Moreover, lysine provides a terminal amino group that is oriented favorably in the α-helix for ligand exchange reactions with the ligand-stabilized metal clusters. Homopolypeptides generally have been used in the practice of the present invention for several reasons. First, certain homopolypeptides are commercially available, such as poly-L-lysine, poly-D-lysine, and poly-DL-lysine (available from Sigma, St. Louis, Mo.). Second, homopolypeptides provide more predictable α-helix formation with the side chains oriented outwardly from the α helix at known, predictable distances. This allows the polypeptide to be designed for a particular purpose.

The peptide also may be a "heteropolypeptide" (having two or more amino acids), or block copolymer-type polypeptides (formed from plural different amino acids with identical amino acids being organized in blocks in the amino acid sequence), as long as such peptides contain groups that that facilitate coupling with metal clusters.

Most amino acids can be used to form suitable homo- or heteropolypeptides. Examples of particularly suitable amino acids include, but are not limited to, naturally occurring amino acids such as lysine, arginine, tyrosine, and methionine; and nonnaturally occurring amino acids such as homolysine and homocysteine.

IV. Placing Scaffolds on Substrates

A. General Discussion

The scaffold simply may be placed on the surface of the substrate, in contrast to more tightly adhering the polypeptide to the substrate such as through electrostatic or covalent bonds. As used herein, the term "substrate" refers to any material, or combination of materials, that might be used to form electronic devices. For example, the substrate may be selected from the group consisting of silicon, silicon nitride, glass, plastics, insulating oxides, semiconductor materials, quartz, mica, metals, and combinations thereof.

Simply placing the scaffold on the surface without considering whether to electrostatically or covalently bind the scaffold to the substrate simplifies the process for making working devices. Placing the scaffold on the surface of the substrate can be accomplished by (1) forming solutions containing the molecular scaffold, (2) placing the solution containing the scaffold onto a substrate, such as by spin coating the solution onto a substrate, and (3) allowing the solvent to evaporate, thereby depositing the solid molecular scaffold onto the substrate surface. In this embodiment, the scaffold may adhere to the substrate by physisorption or chemisorptions.

If simple deposition of the scaffold onto the substrate does not produce a sufficiently robust device, then the scaffold might be more tightly coupled to the substrate. One method for accomplishing this is to use compounds that act as adhesives or tethers between the substrate and the molecular scaffold. Which compounds to use as adhesives or tethers depends on the nature of the substrate and the metal cluster. For example, amino-silane reagents may be used to attach molecular scaffolds to the substrate. The silane functional group allows the tether to be coupled to a silicon, glass or gold substrate. This provides a tether having a terminal amino group that can be used to react with the scaffold to tether the scaffold to the substrate. The terminal amino group also can be used as an initiation site for the in situ polymerization of polypeptides using activated amino acids. Another class of tethers particularly useful for attaching polylysine to substrates is the ω-carboxyalkanethiols ($H-O_2C-R-SH$). DNA may be coupled to mica by the addition of $Mg^{2+}$ ions.

B. Organization of Scaffolds on Substrates

There are many methods for forming organized molecular arrays, particularly linear arrays, on the surface of substrates. One method comprises depositing dilute solutions of scaffold molecules onto substrates. A second method comprises aligning biomolecular scaffolds between electrodes using an electric field. Another comprises growing polypeptide chains between two or more electrodes beginning from an initiation site placed on an electrode. Yet another comprises flow-induced alignment of anchored scaffolds. Each of these approaches is discussed below and/or in the Examples that follow.

1. Deposition from Dilute Solutions

Isolated molecular scaffolds can be prepared by depositing highly dilute solutions (i.e. dilute enough such that the scaffold molecules are separated) onto substrate surfaces.

Alternatively, this can be accomplished by dilution of the molecular scaffold film with an inert, α-helix polypeptide such as poly-γ-benzyl-L-glutamate. See, *Poly(γ-Benzyl-L-Glutamate) and Other Glutamic Acid Containing Polymers*, H. Block (Gordon & Breach, NY) 1983.

2. Aligning Scaffolds in an Electrical Field

A practical method, for providing aligned scaffolds on a substrate employ an electrical field produced between two electrodes. FIG. 1 illustrates saw tooth electrodes 10 comprising electrodes 12–20 that are placed on a substrate by conventional methods, such as electron-beam lithography, UV-photolithography, charged particle beam lithography, thermal evaporation, or lift-off techniques. A solution comprising the scaffold molecules is first formed and then applied to the surface of the substrate having the electrode pattern placed thereon, such as a substrate having the electrode pattern of FIG. 1. α-Helical polypeptides, for example, self-align (pole) in the presence of an applied magnetic field or electrical field (typically 20 $Vcm^{-1}$). See, S. Itou, *Reorientation of Poly-γ-benzyl-L-glutamate Liquid Crystals in an Electric Field, Jpn. J. Appl. Phys.*, 24:1234 (1985). Presumably this is due to their large diamagnetic anisotropy. See also, C. T. O'Konski et al, *Electric Properties of Macromolecules IV. Determination of Electric and Optical Parameters From Saturation of Electric Birefringence in Solutions, J. Phys. Chem.*, 63:1558 (1959).

An electric field is generated between the electrodes, such as the points of the saw tooth illustrated in FIG. 1. This local field between the two points causes the scaffold to align between the points. The solvent is evaporated to provide scaffolds oriented between the electrodes.

Based on the above, it will be apparent that the dipole moment of the scaffold influences whether the scaffold may be oriented between the two electrodes, and the efficiency of the orientation. This is one reason why α-helical polypeptides are particularly useful polypeptides for forming scaffolds. The hydrogen bonds formed in the α-helix all orient in the same direction, thereby aligning the amide and carboxyl groups of the peptide backbone and imparting an overall dipole to the secondary α helical structure. It currently is believed that the dipole is primarily the result of the α helix, and not the side chains.

3. Growing Polypeptides Between Electrodes

In some instances, it may be desirable to use scaffolds to bridge directly between two electrical contacts of interest. This can be accomplished by first placing initiating sites on the electrodes, and then "growing" polypeptides between the initiation sites on the electrodes to form a bridge. One example of how this would be accomplished is to attach a tether to an electrode, the tether having a pendant functional group that is capable of forming peptide bonds when reacted with an activated amino acid. The most likely pendant functional group for this purpose is a 1° amine.

To provide a specific example to illustrate the procedure, a tether comprising an alkyl chain having both a terminal amino group and a terminal sulfhydryl group (i.e., an amino-thiol, HS—R—$NH_2$) is reacted with a gold electrode using conventional chemistry. This covalently attaches the sulfhydryl group of the tether to the metal (i.e., Au—S—R—$NH_2$). The terminal amino group is then used to initiate polymerization of a polypeptide using activated amino acids, perhaps in the presence of an applied field, between the two electrodes. The polymerization is accomplished by supplying activated amino acids for reaction with the primary amine in a chain-growing reaction that serially couples amino acids to the end of the growing chain and regenerates the primary amine for subsequent reaction with another activated amino acid.

Activated amino acids are commercially available and are described in the literature. Activated amino acids useful for growing polypeptides include N-carboxyanhydride (NCA) amino acids. NCA amino acids react with surface-bound initiator sites (e.g., the primary amino groups) to begin a ring-opening polymerization of the NCA-amino acid. See, J. K. Whitesell et al., *Directionally Aligned Helical Peptides on Surfaces, Science*, 261:73 (1993). Whitesell's publication is incorporated herein by reference.

When NCA polymerization is performed under the influence of an electric field applied between two electrodes it is possible to "grow" the polypeptide scaffolds from one electrode to another. One specific example of an NCA amino acid that can be used for this purpose is that derived from N-ε-benzyloxycarbonyl-L-lysine. The amino acid side chains of this compound can be deprotected using trimethylsilyl iodide. Deprotection yields the poly-L-lysine scaffold.

Working embodiments of the present invention generally have used polylysine as the polypeptide useful for forming the molecular scaffold. Polylysine was chosen because it includes a hydrocarbon chain that extends the amino functional group, which can undergo ligand-displacement reactions with the ligand-stabilized metal cluster, out and away from the polypeptide backbone. Thus, two criteria that may be used to select polypeptides for use as molecular scaffolds are (1) the ability of the polypeptide to form α helices, and (2) the presence of side chains that provide functional groups which are metal-cluster stabilizing and capable of undergoing ligand-exchange reactions with the ligand-stabilized metal clusters.

4. Forming Polynucleotide Scaffolds

DNA also is a useful material for forming scaffolds, and has many advantages. For example, it is much easier to form long polynucleotide chains than to form polypeptide chains. Furthermore, DNA provides a more rigid material, and this is a beneficial attribute of scaffold materials. Methods for providing polynucleotide scaffolds also recently have been discovered. See, for example, (1) E. Braun et al., "*DNA Templated Assembly and Electrode Attachment of a Conducting Silver Wire,*" *Nature*, p. 775 (1998); (2) N. Seeman, "*DNA Components for Molecular Architecture,*" *Accounts of Chemical Research*, 30:357 (1997); Qi J., et al. "*Ligation of Triangles Built from Bulged 3-Arm DNA Branched Junctions,*" *J. Am. Chem. Soc.*, 118:6121 (1996); and C. Niemeyer et al. "*DNA as a Material for Nanotechnology,*" *Angewandte Chemie, International Edition in English*, 36:585 (1997). Each of these references is incorporated herein by reference. The Braun reference provides a method for positioning a DNA molecule between electrodes spaced by a particular distance, such as about 10 μm. Double stranded DNA, with single stranded sticky ends, and a pair of electrodes that have single stranded DNA attached thereto that is complementary to the sequence of the sticky ends of the DNA are prepared. Annealing the sticky ends to the single-stranded primers allows coupling of double stranded DNA between two electrodes spaced by a known distance.

There are other methods for positioning DNA scaffolds on a substrate. For example, and without limitation, DNA may be manipulated by: electric fields between two electrodes; attaching one end of a DNA strand to an electrode, and then using solution flow toward another electrode to align the DNA between the two electrodes; using optical tweezers or laser traps to place the DNA in a particular alignment.

V. Decorating Scaffolds With Metal Clusters

Figure 2:
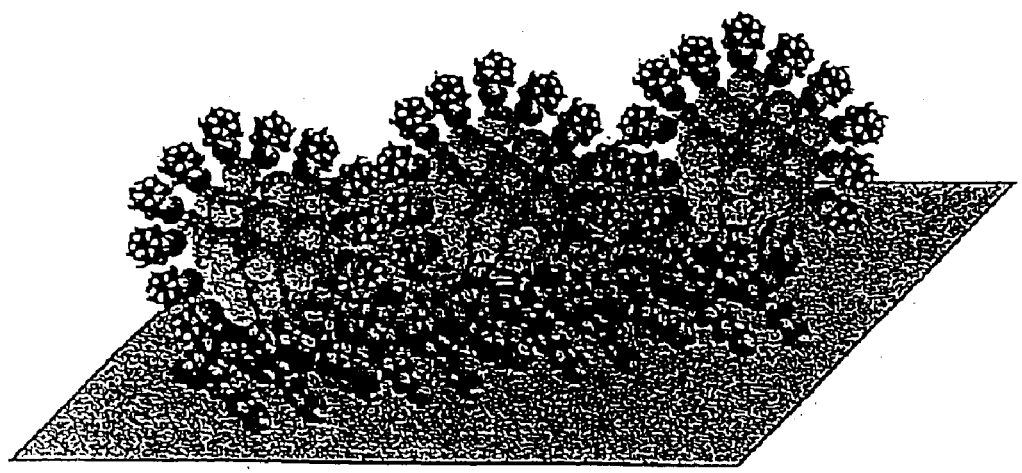
FIG. 2 is a schematic representation of a poly-L-lysine scaffold having thiophenolate-stabilized nanoparticles coupled thereto.

To provide working electronic devices, clusters are coupled to the scaffolds. FIG. 2 provides a schematic representation of a poly-L-lysine that is "decorated" with metal clusters, i.e., the clusters are coupled to the scaffold. A first consideration is whether to decorate the scaffold with clusters prior to or subsequent to placing the scaffold onto a substrate. Although both of these approaches work, there are some disadvantages with decorating the scaffold with the clusters prior to placing the scaffold on the substrate. This approach places clusters on all surfaces of the polypeptide, even those that come into contact with the underlying substrate. This is undesirable for several reasons. For example, such placement of the clusters might interfere with fixing the decorated scaffold to the substrate. And, it places clusters in locations in which they are not needed, and hence uses more valuable monodispersed clusters than needed.

Based on the above, a method which first places the scaffolds onto a substrate, and subsequently decorates the scaffold with clusters is in most instances a more useful approach. This may be accomplished by first forming a solution comprising the ligand-stabilized monodispersed clusters using a solvent that does not dissolve the scaffold. Solvents for this purpose include, without limitation, dichloromethane and hexanes. The ligand-stabilized clusters are then introduced onto the scaffold and allowed to undergo reactions with the scaffold molecules, such as ligand-exchange or acid-base type reactions, thereby coupling the ligand-stabilized clusters to the scaffold. See Example 4 for further details concerning decorating scaffolds with clusters.

The present approach to producing decorated scaffolds also allows for good lateral definition, which is a key feature of the present invention. "Lateral definition" refers to the width of an array. Prior to the present invention, the state of technology was capable of producing lines having a width of about 300 Å. With the present invention, lateral resolution is much improved, and is on the order of about 10 Å. In addition, branched polypeptides offer the possibility of introducing control electrodes and interconnects at the molecular level.

VI. Ultrafast, Ultrahigh Density Switching Devices

This section discusses the steps required to use the decorated molecular scaffolds of the present invention to produce ultrafast, ultrahigh density switching devices. First, a substrate is selected and cleaned. One example of a substrate is a silicon nitride chip or wafer. On top of this substrate would be placed electrical contacts. This could be accomplished using known technologies, such as lithography or thermal evaporation of a metal, such as gold.

Once a substrate is obtained having the electrical contacts placed thereon, a scaffold is then placed on the surface using the techniques described above. Thereafter, the substrate with scaffold is treated with monodispersed, ligand-stabilized clusters to attach such clusters to the scaffold. The organization of scaffold likely determines the particular device being made.

For a switching device, analogous to a transistor, saw tooth electrical contacts, such as those shown in FIG. 1, are deposited onto a substrate and a scaffold then oriented therebetween. This provides two arms of a transistor. A capacitance contact required to provide the third arm of a transistor is imbedded in the substrate underneath the molecular scaffold. Direct electrical contact with this "gate" imbedded in the substrate is not actually required.

Figure 3:
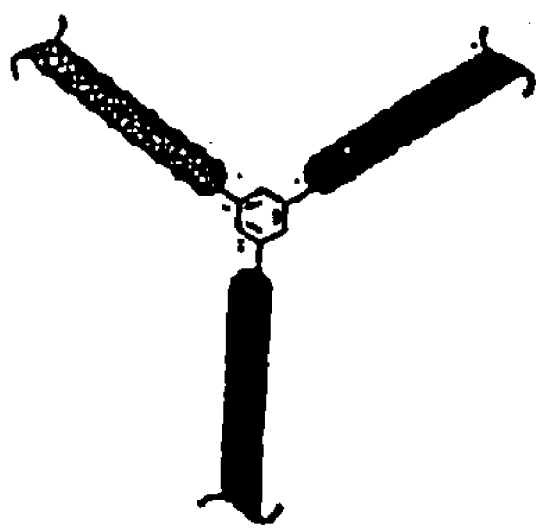
FIG. 3 is a schematic representation of one method for incorporating gate electrodes at the molecular level.

Alternatively, a third contact arm could be incorporated into the template. FIG. 3 is a schematic representation of a scaffold useful for this purpose. For example, a polypeptide of a particular length, e.g., a 25-mer or 50-mer, could first be coupled to an electrode. A branching portion of the scaffold could then be attached, thereby forming an electrical arm, or plural such arms, for further providing single or multiple gate electrodes to the template. The scaffold is then coupled between two electrodes subsequent to the formation of this contact arm, or arms.

The method of the present invention can be used to form a variety of standard circuit components to implement Boolean logic functions. These circuit components include, but are not limited to, AND, NAND, NOR, OR and Exclusive OR gates. Additionally, multiplexers and muliplexer-based circuits can be created and used to implement Boolean logic functions.

VII. Production and use of Phosphine-Stabilized Gold Nanoparticles

The present method provides the first new route to producing phosphine-stabilized gold nanoparticles since their first description nearly twenty years ago. The described route is substantially simpler and safer than the traditional route, which involves the use of diborane gas (see Example 1, below). TEM, XPS and ligand (thiol) exchange reactions respectively reveal that the size, composition and reactivity of nanoparticles synthesized using this new method are comparable to those produced by the traditional route. Additionally, this simple route can produce large quantities of gold nanoparticles capped by tricyclohexylphosphine or trioctylphosphine, producing a novel class of trialkylphosphine stabilized nanoparticles.

First described by Schmid in 1981, phosphine-stabilized gold nanoparticles, commonly referred to as gold 55, paved the way for investigating the properties of metal nanoparticles. The small size and low dispersity of triphenylphosphine-passivated gold nanoparticles continues to make them important tools in the field of nanoelectronics, biological tagging, and structural studies. Recently the ability to exchange thiol ligands onto triphenylphosphine passivated nanoparticles was demonstrated, which enabled the coupling of small size and low dispersity with the stability of thiol-passivated gold. This has allowed investigation of applications that require both high stability and small core size, such as room temperature, Coulomb-blockade-based nanoelectronics. One embodiment of the present method provides a convenient gram-scale synthesis of 1.4 nm triphenylphosphine stabilized nanoparticles that are comparable in both size and reactivity to the traditional gold 55 nanoparticles (Example 8). This route utilizes commercially available reagents and replaces a hazardous reducing agent. The generality of this synthetic method has been explored through the synthesis of previously unknown aliphatic, phosphine-stabilized gold nanoparticles, particularly trialkylphosphine stabilized nanoparticles.

A working embodiment of the synthesis is shown in Scheme 1.

Scheme 1

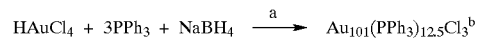

With reference to Scheme 1, "a" refers to reaction conditions, including a toluene:water biphasic solvent system, tetraoctylammonium bromide (see below), and a 5 hour reaction time, and "b" refers to the empirical formula of the resulting product, which is based upon size and atomic composition measurements.

Other suitable solvents for the method include benzene and xylenes. Useful phase transfer catalysts include quaternary ammonium salts of which tetraoctylammonium bromide is only and example.

Phosphine-stabilized gold nanoparticles produced by the method described herein can be used in any applications in which traditionally synthesized gold nanoparticles are used. Such applications include, of course, the construction of scaffold-organized clusters and electronic devises including such clusters described in the present application. In addition, the aliphatic, phosphine-stabilized gold nanoparticles of this invention can be used as biological tags for (e.g., in electron microscopy or for the detection of positive associations on biological microarrays such as cDNA microarrays). Gold particles according to the invention can be used, for instance, to label peptide molecules (Segond von Banchet and Heppelmann, *Histochem. Cytochem.*, 43, 821–827, 1995), proteins (for instance, antibodies or fragments thereof as described in Hainfeld and Furuya, *J. Histochem. Cytochem.*, 40:177–184, 1992); or nucleic acid molecules (such as hybridization probes), or liposomes (Hainfeld., *Proc. An. Mtg, Micros. Soc. Am.*, San Francisco Press, San Francisco, Calif., pp. 898–899, 1996).

In certain embodiments, the gold nanoparticles of the invention can be used in combination with other labels, such as fluorescent or luminescent labels, which provide different means of detection, or other specific binding molecules, such as a member of the biotin/(strept)avidin specific binding family (e.g., as described in Hacker et al., *Cell Vision*, 4, 54–65, 1997).

VIII. Examples

The following examples are provided to illustrate certain particular features of the present invention. These examples should not be construed to limit the invention to the particular features described.

Example 1

This example describes the syntheses of $Au_{55}(PPh_3)_{12}Cl_6$. $Au[P(C_6H_5)_3]Cl$ was obtained from Aldrich Chemical Company. This compound was reduced using diborane ($B_2H_6$), which was produced in situ by the reaction of sodium borohydride ($NaBH_4$) and borontriflouride etherate [$BF_3.O(C_2H_5)$]. $Au[P(C_6H_5)_3]Cl$ was combined with diborane in benzene to form $Au_{55}(PPh_3)_{12}Cl_6$. $Au_{55}(PPh_3)_{12}C_{16}$ was purified by dissolution in methylene chloride followed by filtration through Celite. Pentane was then added to the solution to precipitate a black solid. The mixture was filtered and the solid was dried under reduced pressure to provide $Au_{55}(PPh_3)_{12}Cl_6$ in approximately 30% yield.

Example 2

This example describes the synthesis of $Au_{55}(SC_{18}H_{37})_{26}$. Dichloromethane (~10 ml), $Au_{55}(PPh_3)_{12}C_{16}$ (20.9 mg) and octadecylthiol (23.0 mg) were combined in a 25 ml round bottom. A black solution was produced, and this solution was stirred under nitrogen at room temperature for 36 hours. The solvent was then removed under reduced pressure and replaced with acetone. This resulted in the formation of a black powder suspension. The solid was then isolated by vacuum filtration and washed with acetone (10×5 ml). After the final wash, the solid was redissolved in hot benzene. The benzene was removed under reduced pressure with gentle heating to yield a dark brown solid.

The solid material was then subjected to UV-VIS ($CH_2Cl_2$, 230–800 nm), $^1H$ NMR, $^{13}C$ NMR, X-ray photoelectron spectroscopy (XPS) and atomic force spectroscopy. These analytical tools were used to characterize the structure of the compound produced, and such analysis indicated that the structure of the metal-ligand complex was $Au_{55}(SC_{18}H_{37})_{26}$.

X-ray photoelectron spectroscopy (XPS) data also was collected concerning $Au_{55}(SC_{18}H_{37})_{26}$. This involved irradiating molecules with high-energy photons of fixed energy. When the energy of the photons is greater than the ionization potential of an electron, the compound may eject the electron, and the kinetic energy of the electron is equal to the difference between the energy of the photons and the ionization potential. The photoelectron spectrum has sharp peaks at energies usually associated with ionization of electrons from particular orbitals. X-ray radiation generally is used to eject core electrons from materials being analyzed. Clifford E. Dykstra, *Quantum Chemistry & Molecular Spectroscopy*, pp. 296–295 (Prentice Hall, 1992). Quantification of the data provided by XPS analysis of $Au_{55}(SC_{18}H_{37})_{26}$ made according to this example showed that Au 4f comprised about 67.38% and S 2p constituted about 28.01%+4.17%, which suggests a formula of $Au_{55}(SC_{18}H_{37})_{26}$.

Quantification of XPS spectra gave a gold-to-sulfur ratio of about 2.3:1.0 and shows a complete absence of phosphorus or chlorine. As with $Au_{55}(PPh_3)_{12}Cl_6$, a broad doublet is observed for the Au 4f level. The binding energy of the Au 4f 7/2 level is about 84.0–84.2 eV versus that of adventitious carbon, 284.8 eV. This indicates absence of Au(I) and is similar to binding energies obtained for clusters such as $Au_{55}(PPh_3)_{12}Cl_6$. The binding energy of the S 2p 3/2 peak ranges from 162.4 to 162.6 eV for the series of clusters. These values are shifted to lower energy than those found for free thiols (163.3–163.9 eV) and are close to the values reported for thiolates bound to gold (162.0–162.4 eV). $^1H$ and $^{13}C$ NMR unambiguously rules out the possibility that unattached thiols may be present in the sample.

Thermal gravimetric analysis confirms the Au:S ratio obtained from XPS. On heating to 600° C., ODT-stabilized clusters display a 40% mass loss, corresponding to 26 ODT ligands on an assumed 55-atom gold cluster. This ratio alludes to the retention of a small cluster size. A sample of the larger hexadecanethiol-stabilized gold cluster has been shown to give a 33.5% mass loss, corresponding to from about 95 to about 126 ligands per cluster (diameter=2.4 nm).

Figure 4:
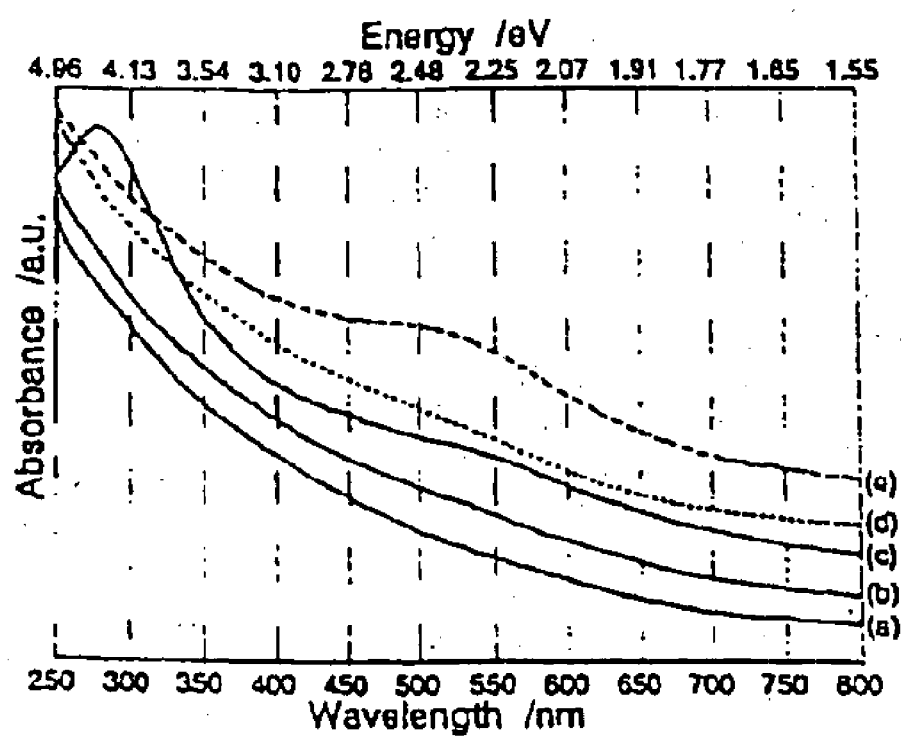
FIG. 4 shows UV-Vis spectra (in methylene chloride solution) of gold clusters with the ligands (a) ODT, (b) Pth, and (c) MBP, and where (d) is starting material and (e) is a sample of larger ODT-stabilized clusters.

Optical spectra of gold colloids and clusters exhibit a size-dependent surface plasmon resonance band at about 520 nm (See FIG. 4). In absorption spectra of ligand-exchanged clusters produced as stated in this example, the interband transition typically observed for small clusters including $Au_{55}(PPh_3)_{12}Cl_6$ was observed. Little or no plasmon resonance was observed, consistent with a cluster size of about 1.7 nm or less. For the ODT-passivated cluster, no plasmon resonance was observed.

Figure 5:
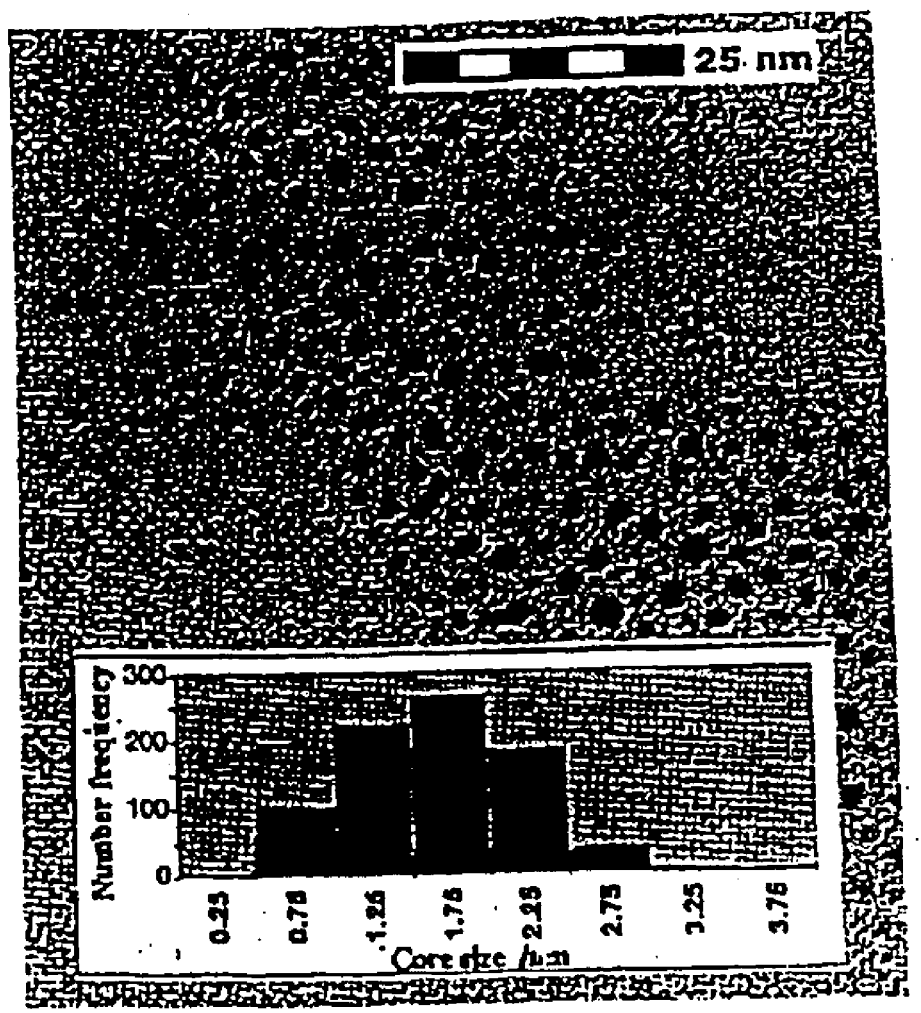
FIG. 5 is a TEM of ODT-stabilized clusters (aerosol-deposited from methylene chloride solution onto a carbon-coated copper grid).

Quantitative size information can be obtained using transmission electron microscopy (TEM). The core size obtained from TEM images of the ODT-stabilized cluster (FIG. 5) is found to be 1.7±0.5 nm and is in good agreement with that obtained from atomic force microscope images.

Atomic force microscopy (AFM) also was performed on the $Au_{55}(SC_{18}H_{37})_{26}$ produced according to this example. The analysis produced a topographical representation of the metal complex. AFM probes the surface of a sample with a sharp tip located at the free end of a cantilever. Forces between the tip and the sample surface cause the cantilever to bend or deflect. The measured cantilever deflections allow a computer to generate a map of surface topography.

Rebecca Howland et al., *A Practical Guide to Scanning Probe Microscopy*, p. 5, (Park Scientific Instruments, 1993). The AFM data showed heights of 1.5 nm for single clusters and aggregates subjected to high force. This corresponds to the size of the gold core clusters. This helped establish that the gold clusters of this example were close to the correct size for forming devices in accordance with the present invention.

In a manner similar to that described above for Example 2, thiol stabilized structures also have been made using 1-propanethiol.

Example 3

This example describes the synthesis of $Au_{55}(SPh-Ph)_{25}$. Dichloromethane (~10 ml), $Au(PPh_3)_{12}Cl_6$ (25.2 mg) and 4-mercaptobiphenyl (9.60 mg) were combined in a 25 ml round bottom. A black solution was produced, and this solution was stirred under nitrogen at room temperature for 36 hours. The solvent was removed under reduced pressure and replaced with acetone. This resulted in the formation of a black powder suspension. The solid was isolated by vacuum filtration and washed with acetone (6×5 ml). The solvent was then removed under reduced pressure to yield 16.8 mg of a dark brown solid.

The solid material was subjected to UV-Vis ($CH_2Cl_2$, 230–800 nm), $^1H$ NMR, $^{13}C$ NMR, X-ray photoelectron spectroscopy (XPS) and atomic force spectroscopy as in Example 2. This data confirmed the structure and purity of the metal complex, and further showed complete ligand exchange. For example, quantification of the XPS data made according to this example showed that Au 4f comprised about 71.02% and S 2p constituted about 28.98%, which suggests a formula of $Au_{55}(S-biphenyl)_{25}$.

AFM analysis showed isolated metal clusters having measuring about 2.5 nm which correlates to the expected size of the gold core with a slightly extended sphere.

Thiol-stabilized clusters as produced above display remarkable stability relative to $Au_{55}(PPh_3)_{12}Cl_6$, which undergoes decomposition in solution at room temperature to give bulk gold and $AuCl[PPh_3]$. No decomposition for the thiol-stabilized clusters was observed, despite the fact that some samples were deliberately stored in solution for weeks. In other tests, the mercaptobiphenyl and octadecylthiol-stabilized clusters (in the absence of free thiol) were heated to 75° C. for periods of more than 9 hours in dilute 1,2-dichloroethane solution with no resultant degradation. Under identical conditions, $Au_{55}(PPh_3)_{12}Cl_6$ is observed to decompose to Au(O) and $AuCl[PPh_3]$ within 2 hours.

Example 4

Figure 6:
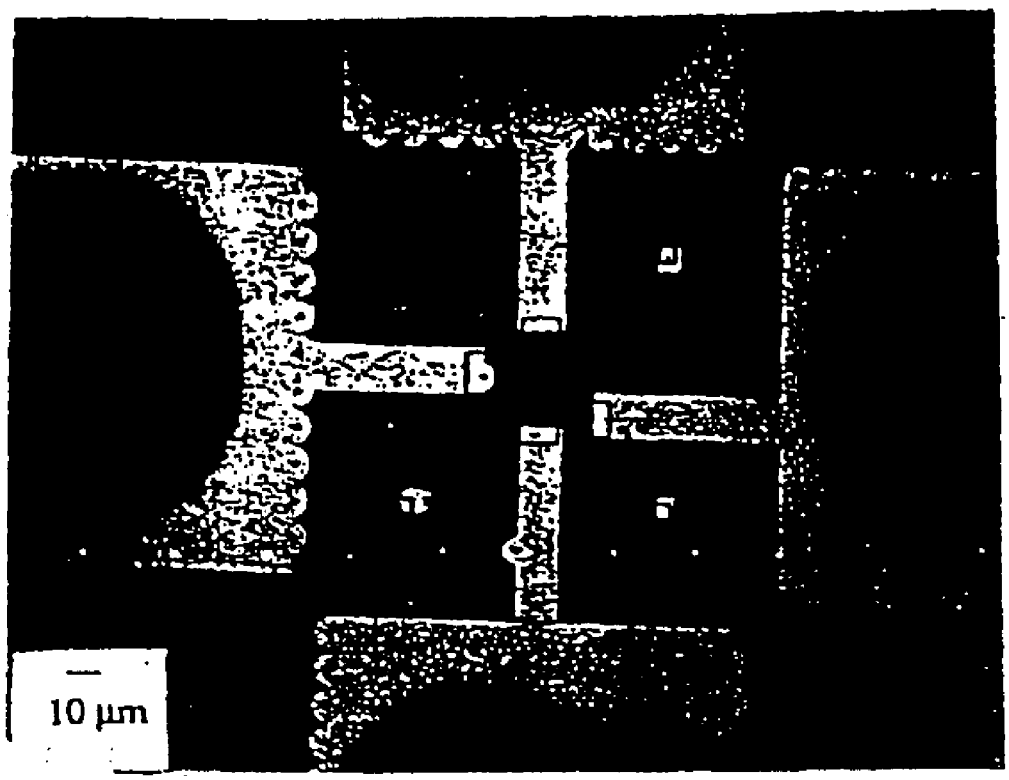
FIG. 6 is an electron micrograph of a patterned gold cluster structure.

This example describes the electron transfer properties of organometallic structures formed by electron-beam irradiation of $Au_{55}[P(C_6H_5)_3]_{12}Cl_6$. This compound was produced as stated above in Example 1. A solution of the gold cluster was made by dissolving 22 mg of the solid in 0.25 mL of $CH_2Cl_2$ and 0.25 mL of 1,2-dichloroethane. A supernatant solution was spin coated onto a $Si_3N_4$ coated Si wafer at 1500 rpm for 25 seconds immediately after preparation. The film was patterned by exposure to a 40 kV electron beam at a line dosage of 100 nC/cm. The areas of the film exposed to the electron beam adhered to the surface and a $CH_2Cl_2$ rinse removed the excess film. This procedure produced well defined structures. See FIG. 6. These structures appeared to be smooth and continuous under SEM inspection. Attempts were made to pattern the material using 254 nm UV lithography, but it was found to be insensitive to this wavelength. The defined structures had dimensions as small as 0.1 μm and AFM inspection measured the film thickness to be 50 nm.

The organometallic samples were spin-coated with PMMA which was electron-beam exposed and developed to define contact regions. Contacts were fabricated using thermal evaporation of 100 nm of gold and conventional liftoff procedures.

DC current-voltage (I-V) measurements of several samples were taken. A shielded chamber, submerged in an oil bath, contained the sample mounted on a clean teflon stage. Rigid triaxial connections were used to connect the sample to a constant DC voltage source and electrometer. The oil bath temperature was controlled from 195 to 350K. Thermal equilibrium was achieved with a 10 Torr partial pressure of He in the chamber. Before electrical measurements the chamber was evacuated to a pressure $\sim 10^{-5}$ Torr. The data showed little temperature drift over a typical four hour measurement sweep. The intrinsic leakage current of the system was measured using a control sample which had the same substrate and contact pad arrangement as the actual samples, but did not have the organometallic between the pads. At room temperature, the leakage current was almost linearly dependent on bias over the range −100 to 100V, and had a maximum value $\leq 100$ fA. While the ultimate resolution of the current measurement was 10 fA, the leakage current set the minimum resolved conductance $\sim 10^{-15} \Omega^{-1}$. Constant amplitude RF signals with frequencies, f, from 0.1 to 5 MHz, were applied to the samples through a dipole antenna at 195K. No attempt was made to optimize the coupling between the RF signal and the sample.

Figure 7:
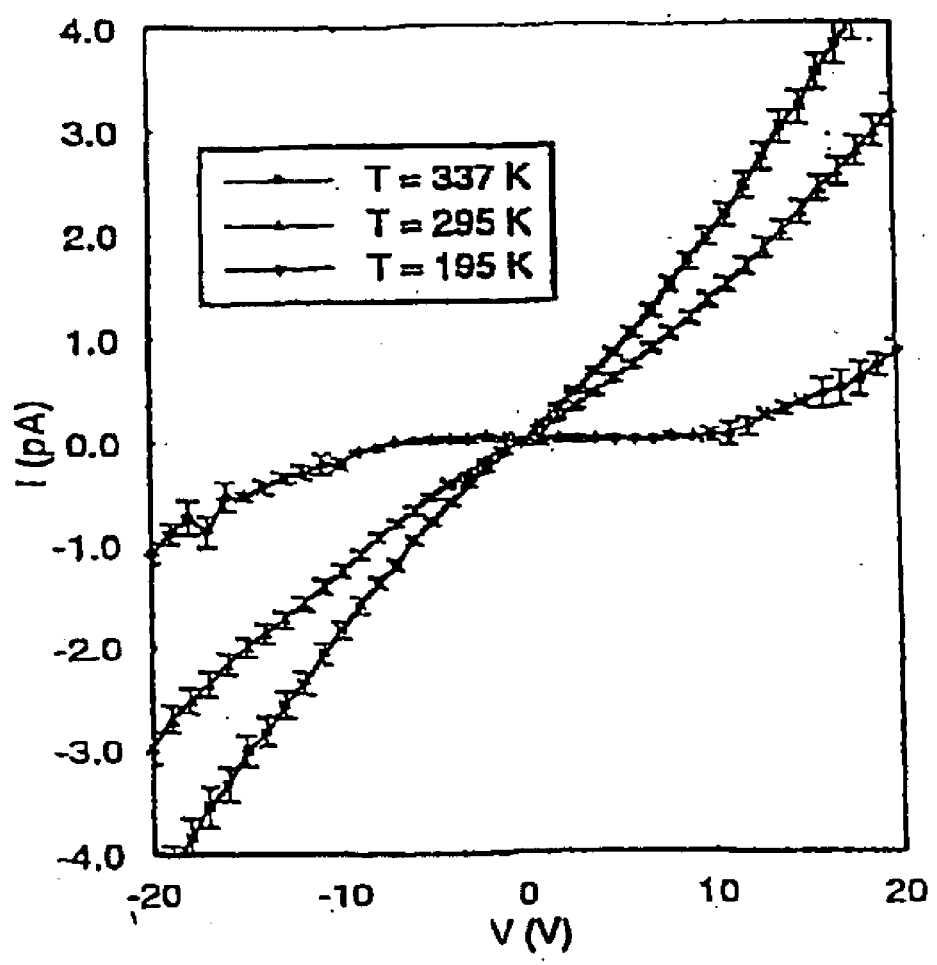
FIG. 7 is a graph illustrating current-voltage (I-V) characteristics of $Au_{55}[P(C_6H_5)_3]_{12}Cl_6$ at temperatures of 195K, 295K and 337K.

Without RF, the I-V characteristics for one sample at several temperatures are shown in FIG. 7. As the temperature was reduced, the low voltage portion of the curve flattened out and the current became indistinguishable from the leakage current. Above an applied voltage magnitude of 6.7±0.6 V, the current increased abruptly. The data illustrated in FIG. 7 establishes that the monodispersed gold clusters can produce devices that operate on the basis of the Coulomb blockage effect. This can be determined from FIG. 7 because one of the curves has zero slope, indicating no current at the applied voltage, i.e., the cluster is blockaded at the particular temperature tested.

Figure 8:
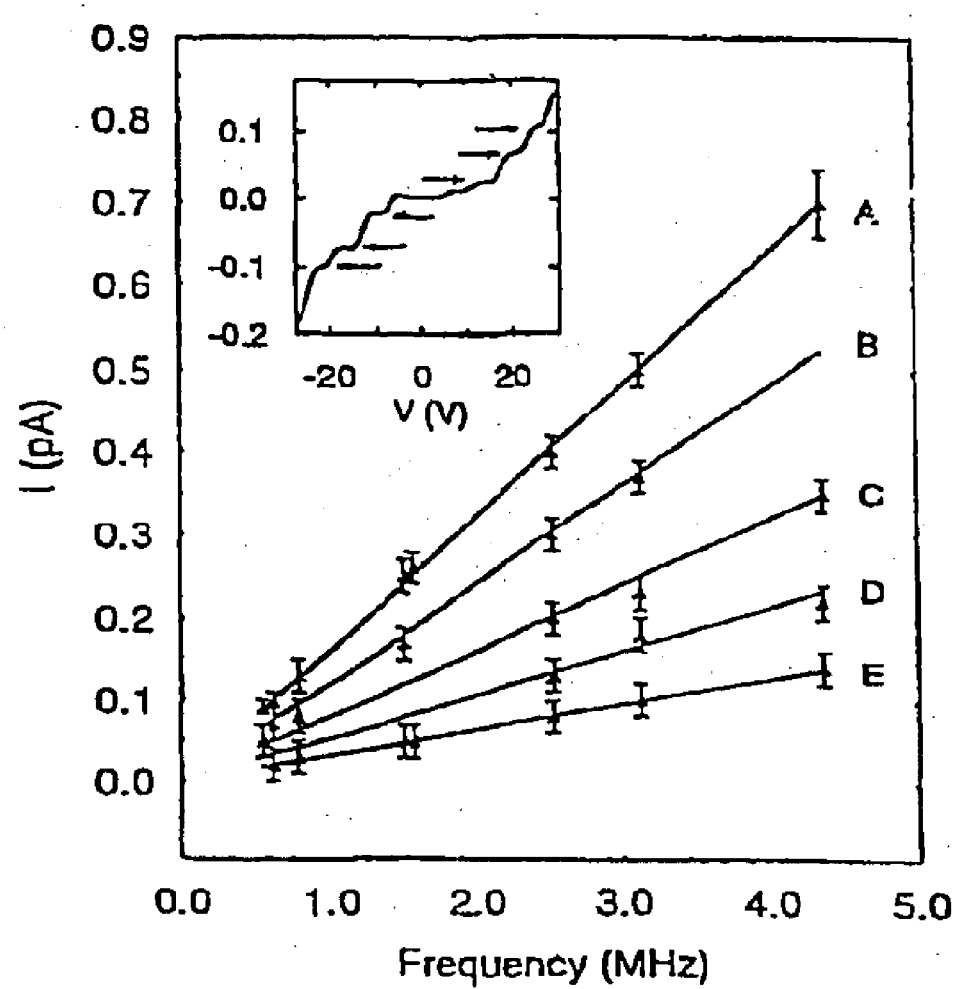
FIG. 8 is a graph illustrating observed current plateaus as a function of the applied frequency at a temperature of 195K, with the inset illustrating the plateau at f=0.626 MHz.

The application of the RF signal introduced steps in the I-V characteristic, as shown in the inset to FIG. 8. FIG. 8 establishes that an applied external varying signal (the frequency of which is provided by the X axis) actually controls the rate at which electrons move through metal clusters made in accordance with the present invention. The current at which these steps occurred was found to be proportional to the applied signal frequency, as shown in FIG. 8. A least squares analysis of the linear current-frequency relationship for the highest current step shown gives a slope $1.59 \pm 0.04 \times 10^{-19}$ C.

The introduction of plateaus in the patterned sample I-V characteristics is similar to the RF response reported in other Coulomb blockade systems. This effect has been attributed to phase locking of single-electron tunneling events by the external RF signal. When the nth harmonic of the applied frequency corresponds to the mth harmonic of the frequency of tunneling in the system, mIle, the current becomes locked to a value I=(n/m)ef. The results obtained suggest that correlated tunneling is present in the samples.

The patterned samples had stable I-V characteristics with time and temperature. Furthermore, as the temperature was raised above about 250K the I-V characteristics developed almost linear behavior up to $V_T$. The conductance below $V_T$ was activated, with activation energies $E_A$ in the range 30–70 meV. One method to estimate the charging energy from the activation energy is to use the argument that the charging energy for one island in a infinite two-dimensional array, $E_C \sim 4E_A$. Assuming current suppression requires $E_c \geq 10$ kT, the sample with the largest activation energy should develop a Coulomb gap below ~300 K. This value is within a factor of 2 of the measured temperature at which clear blockade behavior occurs in the patterned samples. Given the accuracy to which $E_c$ is known, the temperature dependence of the conductance within the Coulomb gap is consistent with the observation of blockade behavior. Using this value of $E_c$, the effective capacitance of a metal core in the patterned array is $3 \times 10^{-19} F < C < 7 \times 10^{-19} F$. These values are close, but larger than the classical geometric capacitance of an isolated Au55 cluster $C = 4\pi \in \in_0 r \sim 2 \times 10^{-19} F$, where the dielectric constant, $\in$, of the surrounding ligand shell is expected to be ~3. The agreement between the two estimates of capacitance supports the notion that the current suppression in the metal cluster arrays is due to charging of individual $Au_{55}$ clusters.

The non-linear I-V characteristic is similar to that of either a forward biased diode or one-/two-dimensional arrays of ultra small metal islands or tunnel junctions. However, the dependence of the I-V characteristic on the applied RF signal is not consistent with straightforward diode behavior. Therefore, the data has been analyzed in the context of an array of ultra small metal islands.

Several reports have discussed the transport in ordered arrays of tunnel junctions that have tunneling resistances greater than the quantum resistance $h/e^2$ and a charging energy significantly above the thermal energy. In this case Coulomb blockade effects introduce a threshold voltage below which current through the array is suppressed. As the applied voltage is increased well beyond threshold, the current-voltage characteristic approaches a linear asymptote with a slope related to the tunnel resistance. With the same temperature and tunnel resistance constraints, Middleton and Wingreen have discussed one- and two-dimensional arrays of maximally disordered normal metal islands where disorder is introduced as random offset charges on each dot. These authors predict current suppression below a threshold voltage and high bias current $I \sim (V/V_T - 1)^\gamma$. Here, the threshold voltage $V_T$ scales with the number of junctions N along the current direction. Analytically $\gamma = 1$ for one-dimensional systems and 5/3 for infinite two-dimensional systems. Numerical simulations of a finite two-dimensional array gave $\gamma = 2.0 \pm 0.2$.

Figure 9:
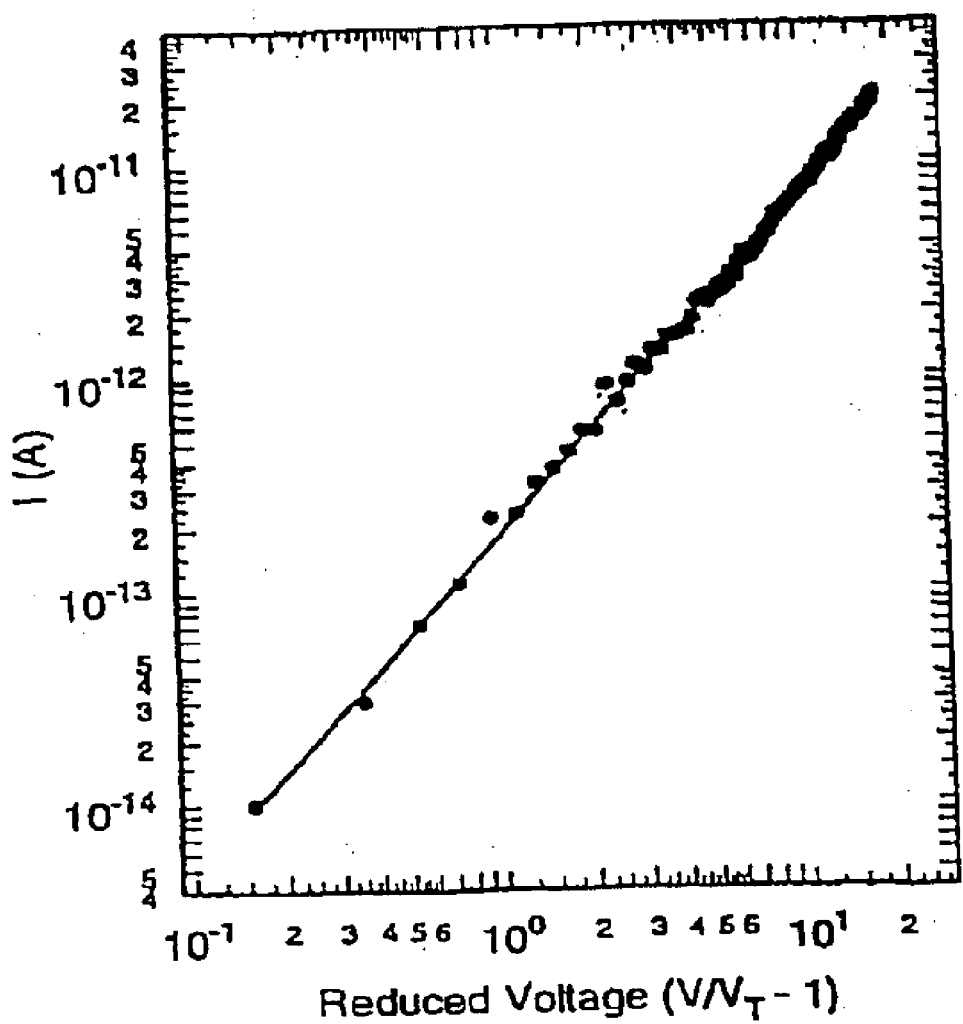
FIG. 9 is a graph illustrating current versus reduced voltage at a temperature of 195K.

While no effort was made to order samples, the data was analyzed using both the ordered and the disordered models. The only consistent analysis was found to be given by the disordered model. In particular, the high bias data did not have the linear asymptote predicted for an ordered system, but did scale as expected for a disordered system, as shown in FIG. 9. FIG. 9 also shows that a two-dimensional array so that sample is propagating through the sample tested along plural parallel paths. Such an arrangement is important for developing memory storage devices. The exponent $\gamma \sim 1.6$ which is closest to the analytical prediction for an infinite, disordered two-dimensional array. From the analysis the magnitude of $V_T \sim 6 \pm 1$ V which is in good agreement with that estimated directly from the I-V data.

The introduction of steps in the I-V characteristics by a RF field is similar to the RF response reported in other systems. This effect has been attributed to phase locking of single-electron tunneling events by the external RF signal. If the applied frequency corresponds to a rational fraction multiple of the frequency of tunneling in the system, I/e, then the current is locked to a value $I = (n/m)ef$, where n and m are integers. Therefore, the linear relationships shown in FIG. 6 between f and I suggests that correlated tunneling is present in the samples. The lowest slope observed is best described with n/m=⅕. For frequencies up to 3 MHz, the current resolution is insufficient to distinguish between the ⅕ and ¼ harmonics. However, at higher frequencies where it should have been possible to distinguish between ⅕ and ¼, the ¼ step was not observed.

At temperatures above about 250K, the I-V characteristic was almost linear up to $V_T$. In this regime the conductance was activated, with activation energies $E_A$ in the range 30 to 70 meV for the samples studied. Similar activated behavior has been reported for tunnel junction systems. It was argued that for an infinite 2D array the charging energy for one island $E_C \approx 4E_A$. Applying this argument to the present system, and assuming current suppression requires $E_C \geq 10$ kT, the sample with the largest activation energy should develop a Coulomb gap below about 300 K. This estimate is within a factor of two of the measured temperature at which clear blockage behavior is seen. Thus, the temperature dependence of the observed current within the Coulomb gap is consistent with the observation of blockade behavior. From the threshold voltage, $V_T = \alpha Ne/C$, and this estimate of $E_C$, $\alpha N$ is approximately 10. The energy $E_C$ can also be estimated if the capacitance of an island is known. The capacitance of an isolated $Au_{55}$ cluster is $C = 4\pi \in \in_o \tau$, where $\tau$ is the radius of the cluster and $\in$ is the dielectric constant of the surrounding medium. The radius of a $Au_{55}$ is 0.7 nm and the ligand shell is expected to have $\in \approx 3$, which $C \approx 2 \times 10^{-19} F$. The Coulomb charging energy, $E_C = e^2/2C \approx 340$ meV which is within twenty percent of the maximum value of $4E_A$ found from the activation data. This result suggests that the current suppression is due to charging of individual $Au_{55}$ clusters.

Given the constraint that steps in the I-V characteristics are only found when $f < 0.1/(R_T C)$, the fact that steps are seen up to f=5 MHz gives the upper limit $R_T < 1 \times 10^{11} \Omega$. The differential resistance obtained from the I-V characteristic well above threshold is anticipated to be $R_{diff} \approx (N/M) R_T$, where M is the number of parallel channels. This estimate yields $N/M \geq 30$. From the sample dimensions and the size of an individual cluster, a close packed array would have N/M~5. This disparity between the expected and experimentally derived values of the N/M suggests that the full width of the sample is not involved in transport. One explanation for the discrepancy in N/M may be that many of the gold cores coalesce during sample fabrication so that transport is dominated by individual clusters between larger regions of gold.

Example 5

Figure 10:
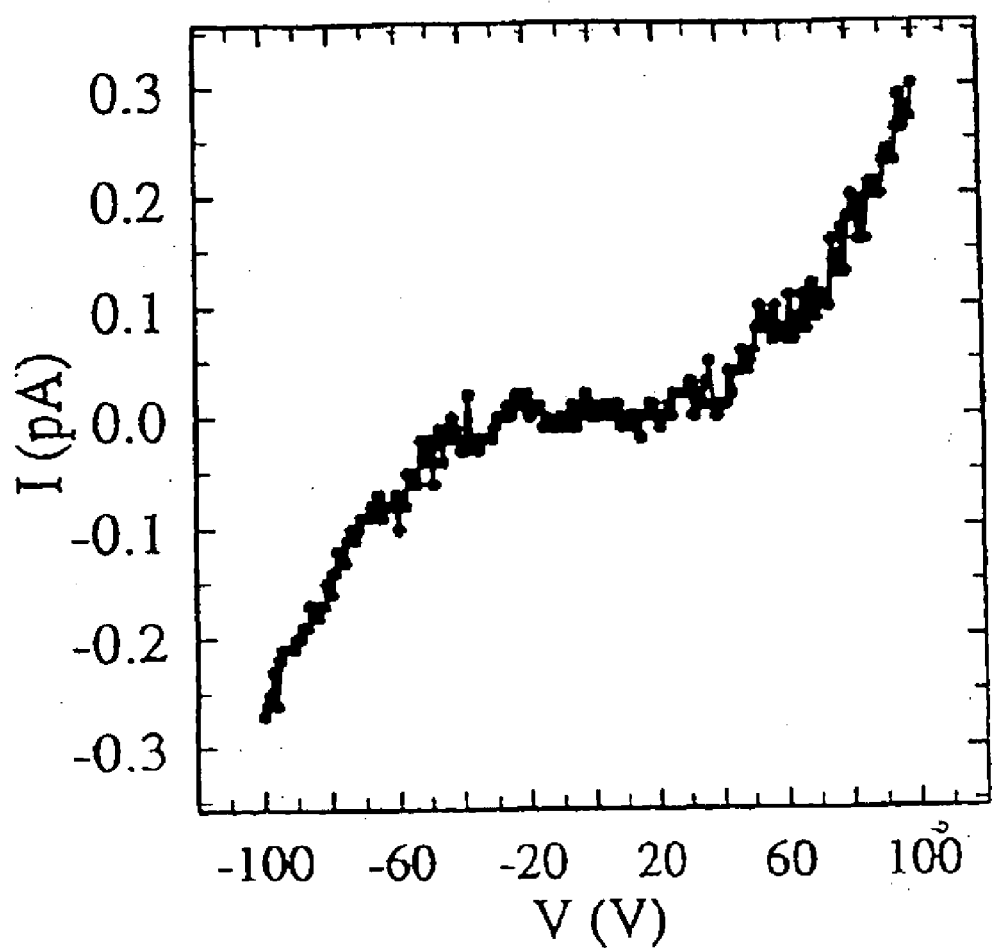
FIG. 10 is a graph illustrating current-voltage (I-V) characteristics of a poly-L-lysine scaffold decorated with 11-mercaptoundeconic ligand-stabilized gold clusters.

This example describes a method for making cluster arrays using poly-L-lysine as the scaffold and 11-mercaptoundeconic ligand-stabilized metal clusters. Prefabricated electrodes were drop-cast with a $2.2 \times 10^{-5}$ mol/l solution of 56,000 amu poly-L-Lysine.HBr in $H_2O/CH_3OH$. After a 20-hour soak in 1% NaOH in nanopure water and a nanopure water rinse, the current-voltage characteristics of the sample were found to be comparable with that of a bare electrode. The polylysine coated electrode was then exposed to a drop of 11-mercaptoundeconic ligand-stabilized gold clusters in DMSO (about 8 mg/1 ml). After about 20 minutes, the sample was subjected to a thorough rinse with DMSO followed by another rinse in methylene chloride. After correcting for the leakage current of the bare electrode, the current-voltage characteristic of the sample were measured, as shown in FIG. 10.

Figure 11:
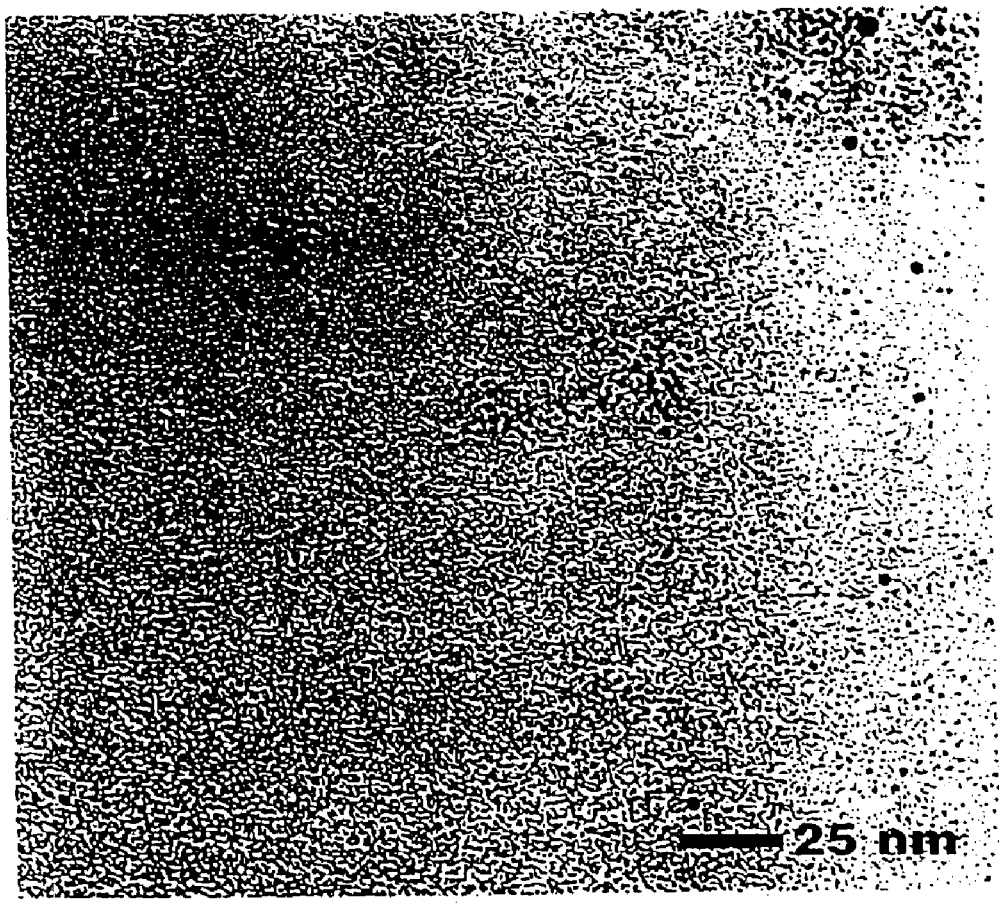
FIG. 11 is a TEM image of a TEM grid having a poly-L-lysine scaffold decorated with 11-mercaptoundeconic ligand-stabilized gold clusters.

A TEM grid was prepared as well using the polylysine scaffold and the 11-mercaptoundeconic ligand-stabilized gold clusters in DMSO. The polylysine solution was drop cast onto TEM grids. A 20-hour soak in 1% NaOH was followed by a nanopure water rinse. The dry TEM grids were then exposed to a drop of 11-mercaptoundeconic ligand-stabilized gold clusters in DMSO. After about twenty minutes, the grids were thoroughly rinsed, first using DMSO and then using methylene chloride. Lines of clusters can be seen in FIG. 11.

Example 6

This example describes how to make electrical connections to metal cluster arrays. Saw tooth interdigitated array (IDA) gold electrodes are used and are made using electron beam lithography. The gap between saw tooth points in the array will be approximately 200–300 Angstroms. An omega-amino alkanethiol will be chemisorbed to the gold surface and subsequently electrochemically desorbed from one set of the IDA fingers. An omega-NHS-ester alkylthiol will be attached to the bare set of fingers. A precursor to poly-L-lysine will be polymerized from the amino-modified fingers toward the NHS-ester fingers where the growing end will be captured. The side chains of the poly-L-lysine chain will be deprotected and treated with carboxy-terminated gold nanoparticles to form the desired one-dimensional array. Gates will be incorporated either under the substrate or as an additional electrode near (above) the surface of the device.

Example 7

This example describes a method for making phosphine-stabilized gold nanoparticles, particularly 1.4 nm (±0.5 nm) phosphine-stabilized gold nanoparticles. Traditional methods for making such molecules are known, and are, for instance, described by G. Schmid (*Inorg. Syn.*, 27:214–218, 1990) and in Example 1).

Scheme 1 (above) illustrates a convenient one-pot, biphasic reaction in which the nanoparticles can be synthesized and purified in less than a day from commercially available materials. Hydrogen tetrachlorolaurate trihydrate (1.11 g, mmol) and tetraoctyl ammonium bromide (1.8 g, mmol) were dissolved in a nitrogen sparged water/toluene mixture (100 mL each). Triphenylphosphine (2.88 g, 11.0 mmol) was added, the solution stirred for five minutes until the gold color disappeared, and aqueous sodium borohydride (2.0 g, 41.0 mmol, dissolved in 5 mL water immediately prior to use) was rapidly added resulting in a dark purple color (this addition results in vigorous bubbling and should be performed cautiously). The mixture was stirred for three hours under nitrogen, the toluene layer was washed with water (5×100 mL) to remove the tetraoctylammonium bromide and borate salts and the solvent removed in vacuo to yield 1.3 g of crude product.

To effect further purification, the resulting solid was suspended in hexanes, filtered on a glass frit, and washed with hexanes (300 mL) to remove excess triphenylphosphine. Washing with a 50:50 mixture of methanol and water (300 mL) removed triphenylphosphine oxide. Each of these washes was monitored by TLC and the identity of the collected material was confirmed by $^1$H and $^{31}$P NMR. Pure samples were obtained by precipitation from chloroform by the slow addition of pentane (to remove gold salts, as monitored by UV-Vis and NMR). After purification, this procedure yielded 644 mg of purified nanoparticle product from 1.35 g of hydrogen tetrachlorolaurate. In contrast, the traditional synthesis yields about 300 mg of purified nanoparticle product per 2 g hydrogen tetrachlorolaurate.

For comparison of these nanoparticles to the products of the traditional synthesis the newly synthesized nanoparticles were analyzed to determine size, atomic composition, and reactivity as described below. The small size of the nanoparticles, which allows for examination of Coulomb blockade phenomena at room temperature, is an important consideration for evaluating the effectiveness of the synthesis.

Direct evidence of nanoparticle size and dispersity is provided by transmission electron microscopy (TEM). TEM was performed on a Philips CM-12 microscope operating at a 100 kV accelerating voltage. Samples were prepared by drop casting dilute methylene chloride solutions onto 400-mesh nickel grids coated with carbon. Images were recorded as photographic negatives, scanned, and processed using NIH image software. A total of 1628 particles were examined from two separate synthetic runs, for the triphenylphosphine nanoparticles. Background noise and agglomerated nanoparticles were removed from the measurements by removing core sizes of <0.5 nm and >3 nm from the analysis.

Figure 12:
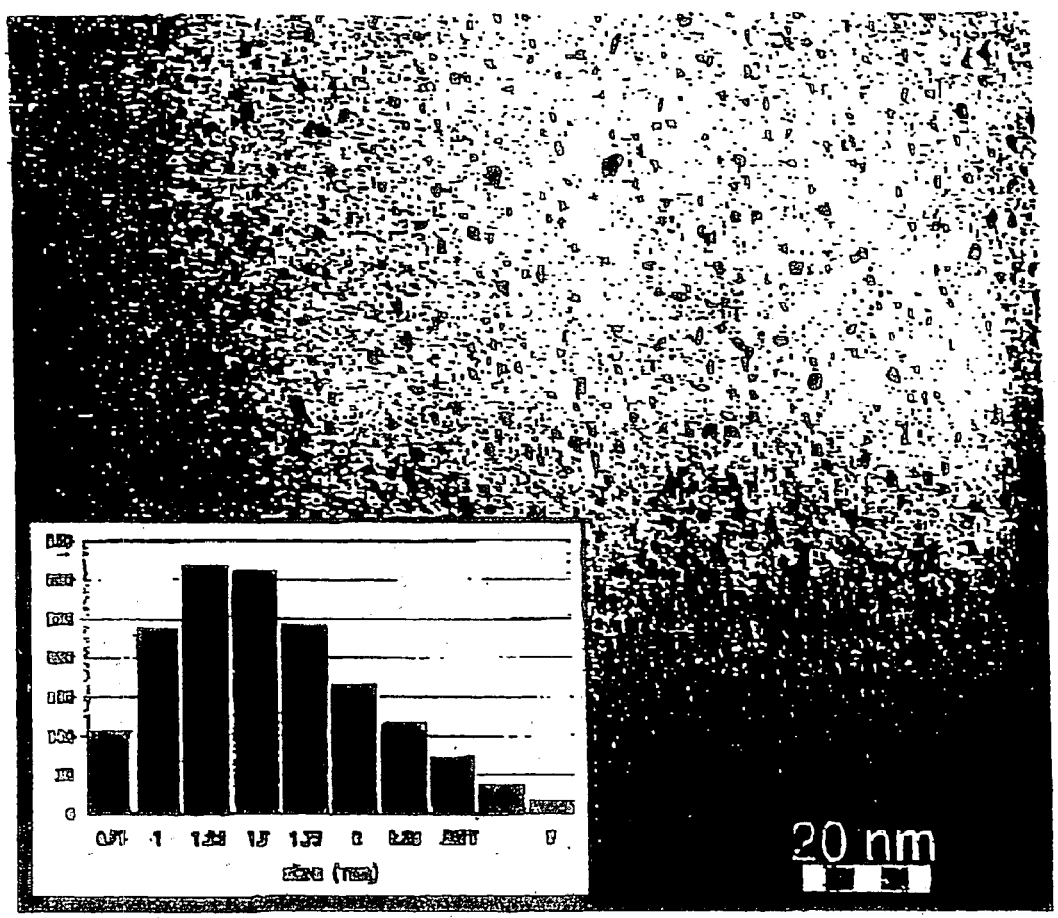
FIG. 12 is a representative TEM image showing nearly monodispersed triphenylphosphine nanoparticle having a particle size of 1.4 nm±0.5 nm.

A representative TEM (FIG. 12) shows nearly monodisperse triphenylphosphine nanoparticles with a size of 1.4 nm±0.5 nm. The FIG. 12 insert is a bar graph showing particle size distribution on this TEM. The x axis of the inset is the size of the particles (measured in nm, starting at 0.75 nm and increasing by increments of 0.25 nm to 3 nm). The y axis of the inset represents the number of particles observed in each size (beginning at zero and increasing by increments of 50 to 350 particles). The size measurements in this TEM compare well with the traditional synthesis, which yields 1.4 nm±0.4 nm particles.

UV/Vis spectroscopy, a technique that is representative of the bulk material, was used to confirm TEM size determinations. UV-visible spectroscopy was performed on a Hewlett-Packard HP 8453 diode array instrument with a fixed slit width of 1 nm using 1 cm quartz cuvettes. The absence of a significant surface plasmon resonance at ~520 nm indicates gold nanoparticles that are <2 nm diameter. UV/Vis spectra of newly synthesized nanoparticles are dominated by an interband transition, with no significant plasmon resonance at 520 nm. This indicates that there is no substantial population of nanoparticles greater than 2 nm in size.

Atomic composition of the nanoparticles was determined using the complementary techniques of x-ray photoelectron spectroscopy (XPS) and thermogravimetric analysis (TGA) allowing further comparison to traditionally prepared nanoparticles. TGA was performed under a nitrogen flow with a scan rate of 5° C. per minute. XPS was performed on a Kratos Hsi operating at a base pressure of $10^{-8}$ torr. Samples were prepared by drop-casting a dilute organic solution of the nanoparticles onto a clean glass slide. Charge neutralization was used to reduce surface charging effects. Multiplexes of carbon, sulfur, and phosphorus were obtained by 30 scans each. Binding energies are referenced to adventitious carbon at 284.4 eV. Data was recorded with a pass energy of 20 eV. XPS spectra provides an average composition of 71% gold, 26% carbon, 2.6% phosphine, and 0.7% chlorine, corresponding to molar ratios of 18 Au:108 C:4.3 P:1 Cl. TGA indicates a mass ratio of 71% gold to 29% ligand, independently confirming the ligand-to-ratio determined by XPS. For direct comparison with the nanoparticles made by traditional methods, an average empirical formula was generated by assuming a core size of 55 gold atoms. Based on this assumption, an average particle produced by the method of the present invention was formulated as $Au_{101}(PPh_3)_{12.5}Cl_3$, in comparison with the $Au_{55}(PPh_3)_{12}Cl_6$ reported by Schmid. While the gold-to-phosphorus ratio matches that of the Schmid nanoparticles, the phosphorus-to-chlorine ratio of 4:1 is double that of the Schmid nanoparticles (2:1). This may be a reflection of the phosphorus-to-chlorine ratio in the starting materials of each reaction.

The reactivity of the nanoparticles to thiol ligand exchange further confirms their similarities to traditional triphenylphosphine stabilized nanoparticles. Using previously reported methods, a number of straight-chain alkanethiol and charged ω-Functionalized alkanethiol ligands have been exchanged onto these nanoparticles. In each thiol-for-phosphine ligand exchange reaction, there is little change in the surface plasmon resonance of the UV/Vis spectra, indicating negligible size changes during the thiol for phosphine ligand exchange. Thus, the newly synthesized nanoparticles are similar in size, atomic composition, and reactivity to the Schmid preparation.

The disclosed methods have enabled the facile exploration of various phosphine ligands that have previously not been explored. Substitution of $PR_3$ for $PPh_3$, and slight modification of the work-up, allows for isolation of alkyl-stabilized nanoparticles in good yield. Trioctylphosphine and tricyclohexylphosphine stabilized gold nanoparticles have been successfully synthesized, which appear to be substantially larger by both UV-Vis. This approach apparently is the first reported synthesis of alkyl-phosphine stabilized gold nanoparticles. Further investigations regarding the effect of the Lewis basicity of the ligand and the steric bulk of the ligand are underway.

This synthesis allows for the expansion of phosphine-stabilized nanoparticle materials. Large amounts of nanoparticle material can be made in a single step using borohydride in place of diborane. Second, this synthesis allows for flexibility in the choice of phosphine ligand that was previously unknown. Variation of ligand-to-gold ratios using the disclosed embodiments of the present invention can be used to achieve unprecedented size control of phosphine-stabilized gold nanoparticles.

Example 8

This example describes a method for determining the size of the nanoparticles made using a process similar to that described in Example 8. Controlling the rate at which the reducing agent, such as sodium borohydride, is added to the reaction mixture, can be used to make nanoparticles materials having desired core diameters, such as a gold core diameter ($d_{core}$<2 nm). The synthesis is the same in every respect as that stated in Example 8 except for the addition rate of the reducing agent ($NaBH_4$). In Example 8, $NaBH_4$ was added rapidly. In this preparation the same quantity of reducing agent was added slowly (over a period of 10 minutes) from a dropping funnel fitted with a ground glass joint and Teflon stopcock. The resultant nanoparticles were shown by UV-visible spectroscopy to have an average diameter of larger than 2 nm.

Example 9

This example describes the formation of gold nanoparticle networks fabricated between the fingers of gold, interdigitated array electrodes having a 15 (or 1.5) or 2 μm gap by electrostatic assembly of carboxylic-acid-modified, gold nanonparticles onto the amino side chains of the biopolymer poly-L-lysine (PLL). The samples were prepared as follows. First, a $2.2×10^{-5}$ mol/l solution of poly-L-lysine-hydrobromide complex (54,000 amu) in 10/90% water/methanol was drop cast onto the electrodes. The electrodes were pre-cleaned using a UV/ozone dry process followed by a rinse in nanopure water. The hydrobromide was removed from the amine side chains of the biopolymer by submerging the cast film in a solution of 1% sodium hydroxide in water for about 20 hours. The 11-mercapto-undecanoic-acid-stabilized, gold nanoparticles were synthesized from Schmid-$Au_{55}$ nanoparticles [see, G. Schmid, *Inorg. Synth.*, 27, 214 (1990)] using ligand exchange. See L. O. Brown and J. E. Hutchison, *J. Am. Chem. Soc.*, 119, 12, 384 (1997). Nanoparticle decoration of the biopolymer was accomplished by placing a concentrated solution of the nanoparticles in dimethylsulfoxide onto the poly-L-lysine film for about 20 minutes, after which it was rinsed in dimethylsulfoxide and then dichloromethane. From the molecular weight, the average length of the poly-L-lysine was determined to be about 30 nm. Therefore, each polymer accommodated about seven or eight nanoparticles.

Current-voltage (I-V) measurements were performed at room temperature with the samples in an electrically shielded vacuum chamber. See, L. Clarke, M. N. Wybourne, M. Yan, S. X. Cai, and J. F. W. Keana, *Appl. Phys. Lett.*, 71, 617 (1997). Control measurements were made on the bare electrodes and again after the PLL had been deposited and deprotonated. The I-V characteristics of the deprotonated PLL and the bare surface were linear (Ohmic) without any structure. Importantly, these two sets of control data were indistinguishable, which shows that to within experimental uncertainty the surface conductance of the glass substrate was unaffected by the deprotonated PLL. In contrast, when decorated with nanoparticles, the samples exhibited pronounced non-linear I-V characteristics. After subtraction of the linear I-V behavior measured before PLL decoration, to within the measurement accuracy the electrical characteristics showed a region of zero conductance at low voltages. See FIG. 13. The onset of current is characterized by a threshold voltage, $V_T$, that was found to be different for different samples. Above the threshold, the current increases and the scaling $I \alpha(V/V_T-1)^\gamma$ describes all sets of data with $\gamma=1.2\pm0.2$. Here the error includes the uncertainty in the current measurement and the spread between different data sets. At voltages above threshold, structure of period DV was observed in the I-V curves of most samples, with the ratio $\Delta V/V_T \sim 2$. This is most easily seen in the conductance, as shown in FIG. 14. For this data the measured threshold voltage is $V_T=12\pm1$ V, and the period of the oscillations is $\Delta V=25\pm3$ V.

Figure 13:
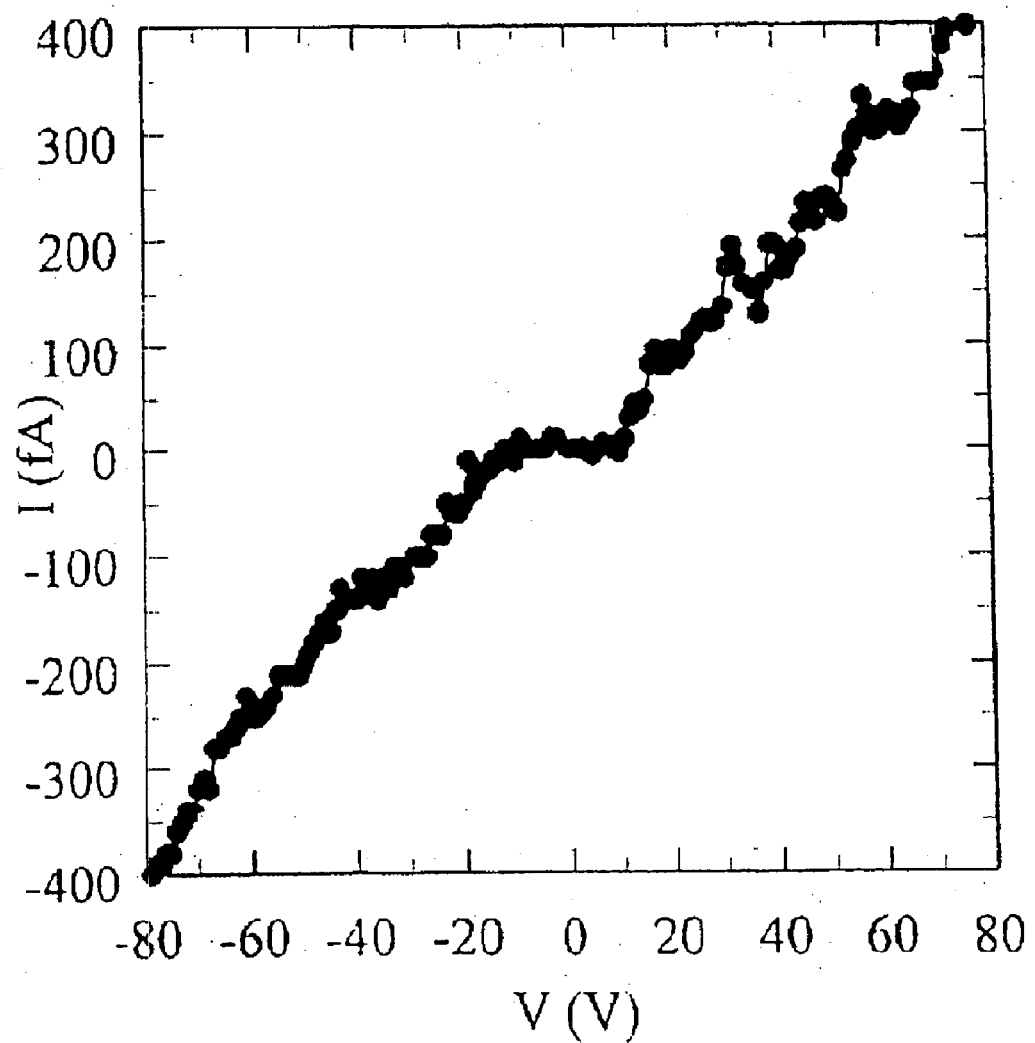
FIG. 13 is a background-subtracted graph of I-V characteristics for PLL films decorated with gold nanoparticles.
Figure 14:
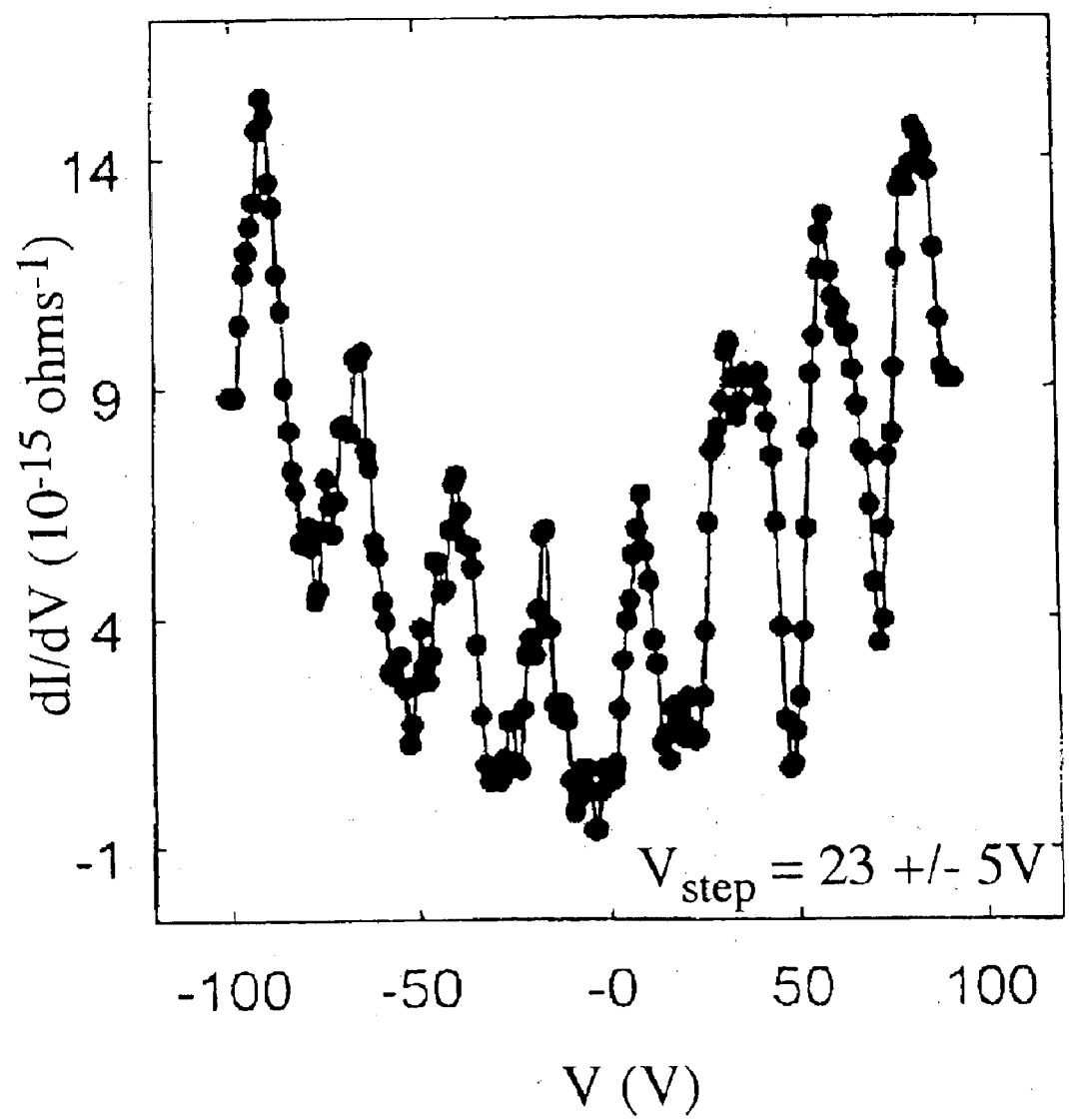
FIG. 14 is a conductance graph of the system of FIG. 13.

Thus, FIGS. 13 and 14 establish stable Coulomb blockade behavior at room temperature. With reference to FIG. 13 and the I-V characteristics of the disclosed systems, above the threshold voltage the current is linear. Moreover, the conductance oscillations show that the systems are defect tolerant.

The value of the scaling exponent γ is indicative of the electronic degrees of freedom in the sample. The values obtained for the tested materials are consistent with single-electron transport in one-dimensional systems where it is predicted that γ~1. These predictions are supported by measurements of the low-temperature transport in one-dimensional chains of lithographically-defined tunnel junctions that found $\gamma=1.36\pm0.1$. Further, the almost linear scaling is distinct from the quadratic scaling reported for thin films containing gold nanoparticles. The current-voltage scaling, threshold behavior and periodic structure are all reminiscent of single-electron behavior in one-dimensional systems, with the region of zero conductance resulting from a Coulomb-gap at the Fermi level. These are remarkable results given the simple method of sample fabrication and the fact that the measurements were made at 300 K. One intriguing feature is the voltage scale of the conductance structure, which is considerably larger than commonly found in other single-electron systems.

Example 10

This example concerns the morphology of nanoparticle/poly-L-lysine (PLL) assemblies. Samples for morphological studies were prepared on mica substantially as described above in Example 10. The assemblies were imaged using tapping mode AFM. The initial, dried PLL.HBr films were found to be smooth with voids probably due to film contraction while drying. During the deprotonation step, PLL is removed and the film becomes more porous, leading to a submonolayer lattice of PLL aggregate. Upon decoration with functionalized nanoparticles, extended, chain-like assemblies were observed. See FIG. 15. Thus, by this method, low dimensional nanoparticle arrays can be made, which allows production of a system having useful electrical properties as opposed to systems comprising monolayers of material.

Figure 15:
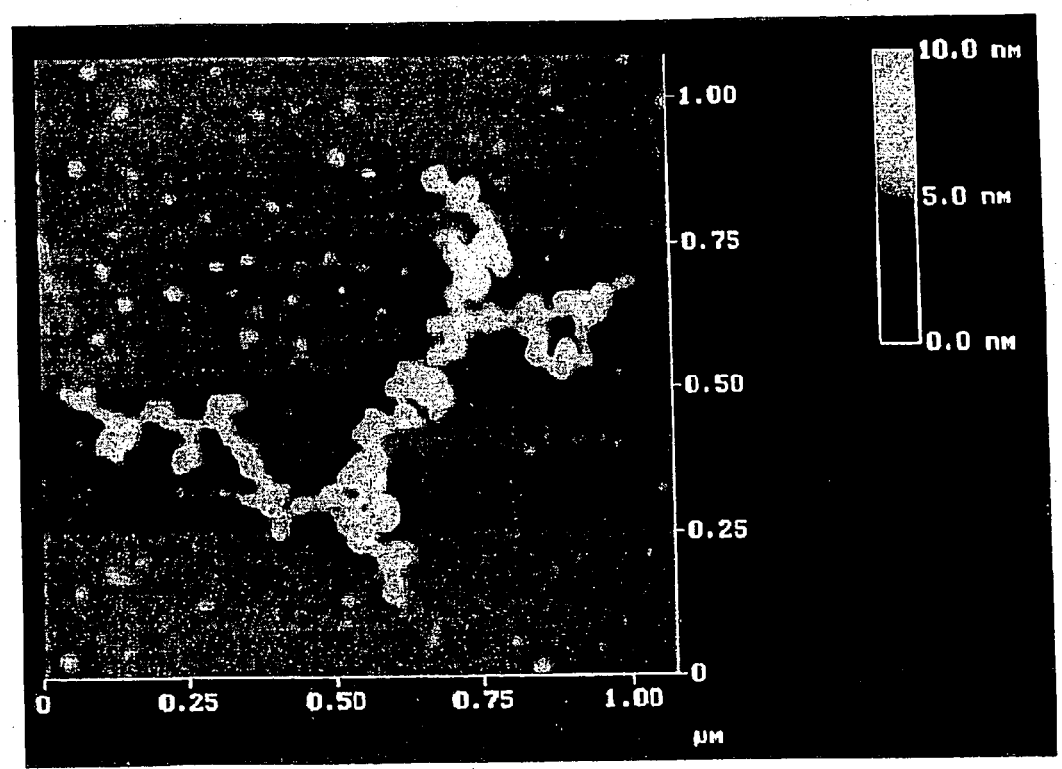
FIG. 15 is a 1×1 μm area showing mercaptoundecanoic acid-stabilized gold nanoparticle arrays formed on mica substrates previously treated with PLL hydrobromide salt and soaked in dilute sodium hydroxide solution until the PLL was no longer detectable by AFM.

FIG. 15 also raises the issue of the effects of disorder and defects. There are two main types of disorder experienced with the disclosed systems, positional disorder and particle size dispersion. FIG. 15 shows that the illustrated embodiment has nanoparticles that are not evenly spaced one from another. This is referred to herein as positional disorder. In traditional semiconductor structures, there is no tolerance for unequal spacing of the metal islands. However, with the small dimensions of the disclosed systems, the electrical properties do not depend on the spacing between cluster. Another potential disorder is particle size dispersion, which can adversely affect the useful electrical properties of the described systems.

The described wet chemical fabrication method produces quasi, one-dimensional structures consistent with the morphology suggested by the current scaling above threshold. The surface coverage of these structures is low, far below that required for a continuous path to be formed between the electrodes. This observation rules out the possibility that bottleneck regions, or a single pathway dominate the electrical behavior. Individual nanoparticles also are found on the surface after chemical fabrication. Their low area density gives an average separation considerably larger than the distance between the nanoparticles forming the extended chains. Thus, the isolated nanoparticles are unlikely to contribute to the overall electrical behavior. The electrical properties suggest single-electron effects in one-dimensional structures and the AFM images show that the fabrication method is capable of producing such structures. However, there is an apparent discrepancy between the disordered nature of the sample seen by AFM (a collection of randomly sized, placed and oriented nanoparticle arrays) and the clearly defined, periodic conductance features in the electrical characteristics that suggest an ordered system. The electrical behavior of randomly oriented nanoparticle arrays that contain defects has been calculated. Periodic conductance features occur despite the presence of defects and that surface conduction in conjunction with conduction through the array explains the large voltage scale found in the data.

Single-electron charging effects are governed by the capacitance between adjacent nanoparticles and the capacitance of each nanoparticle to a ground plane. The nanoparticles can be treated as identical metal spheres of radius 0.7 nm surrounded by a homogeneous ligand shell with a dielectric constant of 3. Including the ligand shell, the minimum center-to-center separation is 4.2 nm. Calculating the capacitance matrix for a row of nanoparticles the interparticle capacitance was determined to be $C_{dd} \approx 0.04$ aF and a capacitance to ground $C_g \approx 0.17$ aF. Thus, the dimensions of these nanoparticle building blocks result in a regime where $C_g > C_{dd}$, which is opposite to that studied in most lithographically defined systems. The capacitance values imply that the total capacitance of a nanoparticle is dominated by $C_g$ and the calculated value shows that the 5 electrostatic charging energy $e^2/2C_g$ is more than an order of magnitude larger than $k_B T$ at 300 K, consistent with Coulomb blockade effects at room temperature.

Numerical simulations of perfect chains confirm that threshold behavior, linear scaling above threshold and a Coulomb staircase can all be expected at room temperature. To simulate the number of conductance peaks observed, a minimum of four particles is required in a chain. While the expected and experimental values of the ratio $\Delta V/V_T$ agree, there is a discrepancy in the absolute voltage values for the threshold and the periodicity. The anticipated value of $V_T \approx e/2C_g = 0.47$ V is more than a factor of twenty smaller than the measured value. Reducing $C_g$ will increase $V_T$. However, assuming that at very small dimensions the capacitance still can be estimated from the geometry of a particle, the reduction in $C_g$ necessary to explain the data would require nanoparticles with unphysically small radii. From this argument it appears that the conduction path must include potential drops that may be the result of contact resistance between the electrodes and the nanoparticle system, surface conduction, weak links within the network itself, or a combination of all three.

The presence of radio frequency (RF) signals and other phenomena, such as quantum size effects and the physical motion of nanoparticles in a field (the shuttle mechanism) also can introduce conductance features. RF signals applied to the sample had no perceivable affect on the conductance structure. Quantum size effects are weak at room temperature and the energy level structure is highly dependent on the structure of the nanoparticles, the ligands and the coupling between particles. Thus, it seems unlikely that resonant tunneling through discrete electronic levels is the cause of the regularly spaced structure we observe. A shuttle mechanism is ruled out because it predicts structure equally spaced in current rather than in voltage as found with the present systems. For the I-V characteristics measured, this mechanism also would require vibrational frequencies that are much lower than is reasonable for the properties of the ligand.

Given the preparation method and the large area (~3 mm$^2$) sampled by the IDA electrodes, disorder and spatial averaging are expected in the samples. The types of disorder expected to have the greatest influence on the electrical properties are variations in core size that influence $C_g$ and the particle-particle spacing (positional disorder) that affects $C_{dd}$. In addition, the effects of particle chain length and chain orientation must be considered. Numerical simulations were used to explore these effects individually and in combination. Chains of between four and nine particles whose core radii were randomly dispersed by up to ±30% (the measured value) showed conductance structure that was periodic to within the measurement uncertainty (±12%). For chains that contain ten or more particles, the uncertainty in the periodicity was much larger than measured. Similarly, when the radius dispersion was increased to ±50% the position of the conductance peaks was found to change significantly and the ratio $\Delta V/V_T$ deviated markedly from a value of two. Dispersion in $C_{dd}$ due to a distribution of particle-particle spacings was found to have little effect on the features. This is not surprising for a system in which $C_g > C_{dd}$ since the conductance is relatively insensitive to the inter-particle capacitance. From this analysis it appears that individual, one-dimensional chains containing less than ten particles with ±30% radius variation can support Coulomb staircase behavior.

When many chains are in parallel the periodicity is maintained provided the chain lengths have a narrow distribution, implying that the samples contain chains of a well-defined length. This length may arise from individual PLL chains that, based on their molecular weight, can accommodate seven or eight nanoparticles. Given length uniformity, angular averaging over all possible orientations of a perfect chain between the electrodes does not remove the conductance peaks, but does broaden them and increases the conductance in the valleys between peaks. When core size dispersion (±30%) and orientation averaging are combined, the simulations still predict periodicity in the conductance. For these simulations 756 chains each having a different randomized set of capacitances and a different orientation were used. Interestingly, even with this degree of averaging, residual conductance periodicity is still found. While a direct comparison with the measured data cannot be made, it appears as if the amount of disorder used in the simulations overestimates the actual degree of disorder in the samples.

Finally, note that the nature of the current path and the fact that the measured voltage scale of the Coulomb blockade structure disagrees with the value determined from the capacitance. The conduction process must involve both the chains and the surface of the substrate. The origin of the surface conductance is likely a thin water layer, which is known to have Ohmic behavior and is expected given the wet chemical preparation method. The surface conductance is the background that is removed from the data and is the means by which chains, arranged randomly on the surface, are electrically connected. Once the potential drop across a chain reaches the threshold value, the chain will come out of blockade and become part of the conduction path. Given that the chains are short compared to the inter-electrode spacing and that there does not appear to be a continuous path between the electrodes, the point at which a chain begins to conduct is a particular fraction of the applied voltage: that is, the surface conductance behaves in the manner of a potential divider which provides an explanation for the difference between the predicted and observed scales. It is known that the interparticle spacing in ordered arrays of nanoparticles plays a role in the nature of the electrical transport. In certain embodiments of the arrays described herein the ligands provide a core separation that suggests electron hopping is the process responsible for charge transfer. In this case, transport will be dominated through chains that have the lowest potential barriers between nanoparticles. Defects are expected to increase the potential barrier. Hence, chains that have the fewest missing or misplaced nanoparticles (defects) will govern the transport properties.

The wet chemical process has been used to produce extended nanoparticle arrays on biopolymer templates between electrode pairs. The I-V characteristics show clear evidence for single-electron charging effects in transport that is limited to one-dimension. From the computed capacitance values and numerical simulations the chains likely contain between four and nine nanoparticles and that the I-V behavior of an ensemble of chains interconnected by the surface conduction of the substrate is tolerant toward variations of chain orientation, core size and inter-particle spacing. The measurements reported here used indirect electrical contact to an ensemble of nanoparticle arrays. This suggests that similar contact techniques which avoid alignment between electrodes and nanoparticles will be useful in their future electrical characterization and application.

Example 11

This example concerns using DNA as a scaffold for receiving nanoparticles. Thin macroscopic gold or silver pads are deposited onto freshly cleaved mica through a shadow mask that defines contacts. Vacuum annealing is used, where necessary, to produce extremely flat metal surfaces. Silver is preferred because it does not interfere with the detection of gold particles on the surface by XPS. Purified lambda DNA (a Hind III digest from New England BioLabs, Inc consists of eight fragments of defined length, ranging from 42–7,800 nm) is deposited onto the mica substrate in the presence of $Mg^{2+}$ that serves to bind the DNA to the mica such that the DNA double strands are extended along the surface. Some of these strands rest partially on the gold pads and partially on the mica surface. These samples, after rinsing and drying, are used for control experiments and as templates for assembling the gold nanoparticles. Individual undecorated double-stranded DNA chains are identified by AFM. A survey of the periphery of the electrode contact pads reveals the number of appropriate strands on the surface and aids in optimizing the deposition conditions.

Functionalized nanoparticles for assembly on the DNA templates are prepared as described herein. For example, one embodiment of such a method was used to make functionalized, 1.5 nm diameter gold nanoparticles. The reaction conditions were: a) two-phase mixture of toluene and water, one equivalent tetraoctylammonium bromide, 10 equivalents, sodium borohydride, and b) either a single-phase ligand exchange with an organic solution of a thiol or a two-phase exchange between Au-TPP in organic solvent and a water-soluble thiol in aqueous solution.

Example 12

This example describes a method for making an intentionally crossed junction of DNA-templated, one-dimensional, nanoparticle assemblies. DNA is first attached to an electrode, such as by using a thiol linkage. The DNA is then correctly aligned by flow-induced alignment of the DNA strand. The DNA strand is bound to the mica surface, such as by using $Mg^{2+}$. Cationic nanoparticles are deposited onto the DNA template, and the DNA is attached to the adjacent electrode. A second DNA strand is aligned by flow-induced alignment orthogonal to the first DNA strand. The second DNA strand binds to the cationic nanoparticles on the first DNA strand. Additional cationic nanoparticles may be deposited onto the new DNA strand to form an intentionally crossed junction of DNA-templated, one-dimensional nanoparticle assemblies.

In another embodiment, complex DNA architectures, such as Holliday junctions are used as the scaffold for creating patterns of nanoparticles between electrodes. Assembly of branched structures on electrode patterned surfaces provide a method for assembling gates of electronic dimensions. For example crossed strands of nanoparticles, where the two strands are produced from nanoparticles of differing radii, may be used to produce a molecular-scale gate for the strand having the smaller radius nanoparticles.

Example 13

Figure 16:
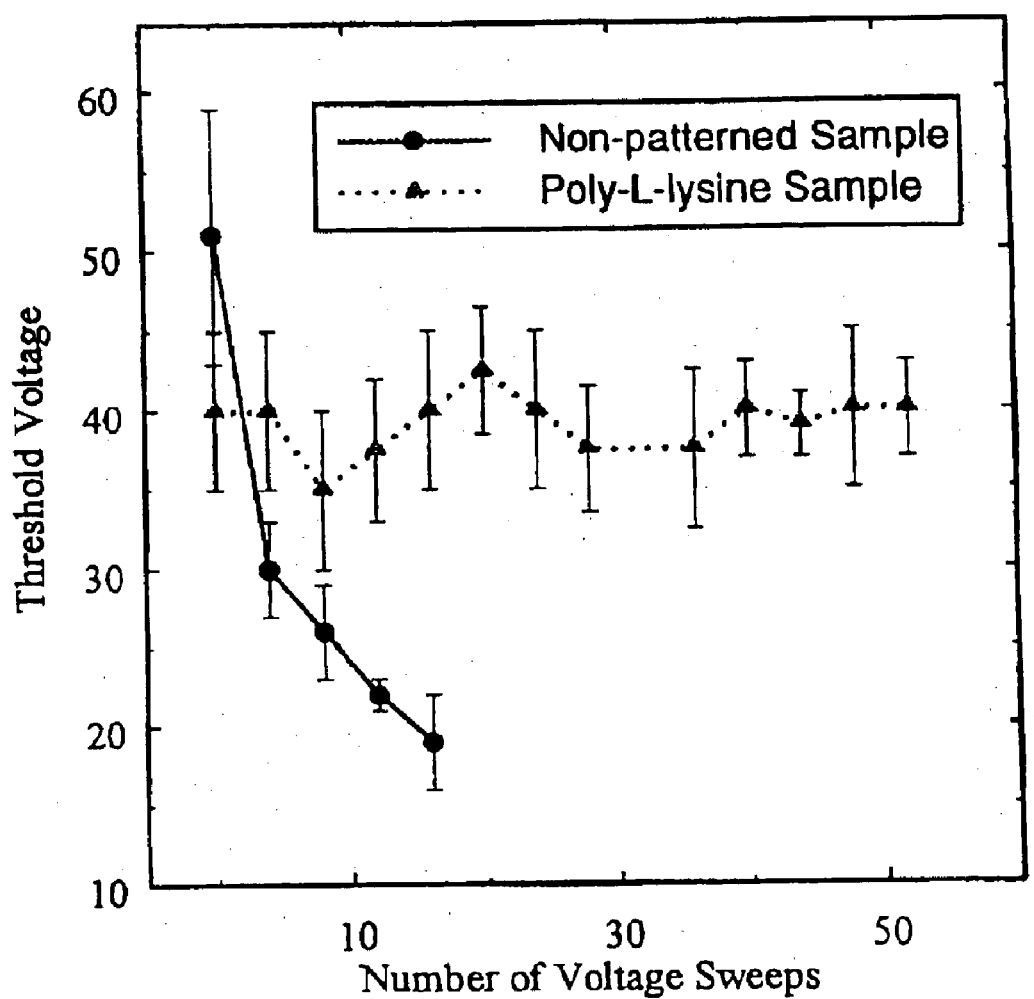
FIG. 16 is a graph of voltage sweeps versus threshold voltage for a non-patterned sample versus a poly-L-lysine-patterned sample.

FIG. 16 illustrates that the poly-L-lysine templated sample has a stable and reproducible voltage response, and that the response of the system does not decay over time. In contrast, when a template is not used and a non-patterned system formed, the response decays. Thus, the template stabilizes the voltage response, likely because the particles are in fixed positions, and hence such systems are electrically more stable than systems that are not patterned.

The disclosed embodiments provide a novel approach to providing structures having well defined electrical properties. Coulomb blockade at room temperature is routinely observed in these systems, and the Coulomb blockade response is stabilized using biopolymer templating. And, single-electron charging effects in one-dimensional pathways are remarkably tolerant of defects and disorder.

The present invention has been described with reference to preferred embodiments. Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. An electronic device that operates at or about room temperature based on the Coulomb blockade effect, comprising:
   a first cluster comprising a metal cluster core having a radius of between about 0.4 nm and about 1.8 nm; and
   a second such cluster physically spaced apart from the first metal cluster at a distance of less than about 5 nm, where the physical separation between the first and second clusters is maintained by the clusters being coupled to a biomolecular scaffold.

2. The electronic device of claim 1, comprising first and second biomolecular scaffolds, each with coupled clusters, where the first and second scaffolds intersect.

3. The electronic device of claim 1, where the device exhibits a linear increase in the number of electrons passing between the first and second clusters as the potential difference between the two clusters is increased above a threshold value.

* * * * *